(12) United States Patent
Colin et al.

(10) Patent No.: US 7,537,730 B2
(45) Date of Patent: May 26, 2009

(54) REACTION CARD AND USE OF SAME

(75) Inventors: Bruno Colin, Marcy l'Etoile (FR); Cécile Paris, Marcy l'Etoile (FR); Bernard Limon, Rignat (FR); Patrick Broyer, Villeurbanne (FR); Charles Rogers, Halifax, MA (US)

(73) Assignee: Biomerieux S.A., Marcy l'Etoile (FR)

( * ) Notice: Subject to any disclaimer, the term of this patent is extended or adjusted under 35 U.S.C. 154(b) by 674 days.

(21) Appl. No.: 10/362,873

(22) PCT Filed: Aug. 27, 2001

(86) PCT No.: PCT/FR01/02671

§ 371 (c)(1), (2), (4) Date: Nov. 3, 2003

(87) PCT Pub. No.: WO02/18823

PCT Pub. Date: Mar. 7, 2002

(65) Prior Publication Data

US 2003/0186295 A1  Oct. 2, 2003

(30) Foreign Application Priority Data

Aug. 28, 2000 (FR) .................................. 00 10978

(51) Int. Cl.
*F16K 35/00* (2006.01)
*B01L 11/00* (2006.01)
*G01N 21/00* (2006.01)
*F17D 1/16* (2006.01)

(52) U.S. Cl. .......................... 422/58; 422/101; 422/103; 251/115; 137/14

(58) Field of Classification Search .................... 422/58, 422/103, 101; 251/115; 137/14
See application file for complete search history.

(56) References Cited

U.S. PATENT DOCUMENTS

| 5,726,026 | A | 3/1998 | Wilding et al. ............. 435/7.21 |
| 5,856,174 | A | 1/1999 | Lipshutz et al. .......... 435/286.5 |
| 6,074,827 | A | 6/2000 | Nelson et al. ................... 435/6 |
| 6,537,501 | B1 * | 3/2003 | Holl et al. .................... 422/101 |

(Continued)

FOREIGN PATENT DOCUMENTS

FR          2 762 092        10/1998

(Continued)

*Primary Examiner*—Jill Warden
*Assistant Examiner*—Lore Ramillano
(74) *Attorney, Agent, or Firm*—Drinker Biddle & Reath LLP

(57) ABSTRACT

A reaction card (1) having a body, a front surface (62) and a rear surface (63) defined by an edge (68), at least one inlet (2, 3, 4 and/or 5) and at least one outlet (7 and/or 8), connected by a network of channels (64) constituting at least one reaction path for at least one fluid which is directed via valves (11 to 36 and/or 61); each valve includes a flexible film (67) which can be deformed to allow fluid passage, the film being fixed on the card's rear surface at a peripheral indentation of an assembly of channels associated with the valve; the card includes channels flush with at least one of its surfaces, the channels being of two different cross-sections, a small cross-section serving as a reaction compartment; each front or rear surface is delimited by at least one film (48, 49, 65, 66 and/or 67).

18 Claims, 9 Drawing Sheets

U.S. PATENT DOCUMENTS

| | | | | |
|---|---|---|---|---|
| 6,615,856 B2 * | 9/2003 | McNeely et al. | ............... | 137/14 |
| 6,902,706 B1 * | 6/2005 | Colin et al. | .................. | 422/103 |
| 6,979,315 B2 * | 12/2005 | Rogers et al. | ................ | 604/151 |
| 2002/0055167 A1 * | 5/2002 | Pourahmadi et al. | ...... | 435/287.2 |
| 2003/0027352 A1 * | 2/2003 | Hooper et al. | .............. | 436/169 |

FOREIGN PATENT DOCUMENTS

| | | |
|---|---|---|
| FR | 2 795 476 | 12/2000 |
| WO | WO 97/27324 | 7/1997 |
| WO | WO 98/49344 | 11/1998 |
| WO | WO 00/13795 | 3/2000 |

* cited by examiner

Coupe A-A

Coupe B-B

REACTION CARD AND USE OF SAME

This application is a U.S. National Stage of International application PCT/FR01/02671, filed Aug. 27, 2001.

DESCRIPTION

This invention concerns a reaction card to be used for conducting chemical and/or biological reactions. It also concerns the use of such a card to purify and amplify nucleic acids and to detect them.

The background art is given in patent U.S. Pat. No. 4,585,623 which describes an apparatus for the rapid execution of chemical or immunochemical assays in a single unit. This apparatus comprises a moulded plastic body (which can be miniaturized) with several reagent-containing tubes, one tube containing the sample, and another, smaller tube to receive the reaction. Since each tube is fitted with a plunger, the apparatus can be introduced into a programmable machine.

Even though it can be miniaturized, this apparatus is still relatively bulky because space has to be provided for said apparatus as well as the various connecting rods to drive the plungers. Moreover, only one reaction can be conducted with such an apparatus. If more than one reaction has to be carried out, the corresponding number of apparatuses will be needed as well as extra time for loading each with the appropriate reagents and samples.

Document WO-A-97/27324 concerns a cassette for conducting several parallel reactions which includes an inlet opening and an outlet opening for the transfer of one or more samples to be introduced into the cassette. Some parts of the cassette are constructed in a particular way (the Bursapak chamber, piston valve and ball valve) so that a channel is kept open or closed when pressure is exerted continuously from the inside or outside. The Bursapak chambers are sometimes associated with hydrophobic filters which allow the progression of a fluid to be blocked.

However, this construction features a major drawback which resides in the valve structure of the Bursapak chambers. These all include films which must be preformed prior to their installation on the reaction card. This pre-forming operation enables each Bursapak chamber to be maintained closed in rest position (FIGS. 2A and 2B). This chamber can be opened by means of an interior action (FIG. 2C), such as, for example, by an increase in the pressure of a fluid contained in the reaction card, or by means of an exterior action (FIGS. 2D and 2E), such as an increase in the pressure of a piston or other element against the preformed film, for example. This preforming of each film must thus be undertaken before it is installed on said reaction card. The cost of fabrication, storage and transport of such films is definitely greater than for films which remain flat. In addition, this does not facilitate the fabrication, storage and transport of reaction cards that are so equipped. Finally, the convex shapes of these films can be damaged more easily, which can lead to leakage or errors during the subsequent use of said cards.

Document WO-A-97/02357 describes a nucleic acid diagnostic apparatus which is similar to the previous cassette in terms of complexity. FIG. 2b presents a valve having a great number of components.

This apparatus thus essentially has the same drawbacks as WO-A-97/27324.

Patent application WO-A-99/33559 proposes a card or cartridge for separating a specific constituent, such as nucleic acids, present in a sample. To this end, it features a number of compartments and channels. From the start, these compartments contain all the liquids (elution liquid, wash solution, for example) that will be used. Fluid movements are controlled by valves placed irregularly within the card, and by fluid sensors. These valves operate as fluid diodes which allow a fluid to flow in one direction only. To do this, they use magnetic disks which can be moved from the outside. The sensors are electrically connected to the outside or to a microprocessor inside the card.

This type of card is particularly complex as its body consists of a sandwich of several stacked elements; refer to the fluid diodes in this respect. In addition, there must be a hermetic seal between these various superimposed elements. In addition to the sensors, the card includes electric wires, fluid diodes operating with magnets, and even a microprocessor. Fabrication cost is thus prohibitive, and all of these electrical and magnetic components can influence the internal operation of said card. A card of this type is thus not very well adapted to micro-fluid based technology. The presence of fluids inside the card thus limits storage time or requires that an experienced handler introduce these fluids. Operational flexibility is thus rather limited.

As provided by the invention, a reaction card is proposed which addresses all of these problems. Such a card proposes biological analysis of one or more ligands, requiring the use of one or more anti-ligands for their detection and/or quantification. One example of an application of the test methods concerns immunoassays, whatever their particulars and whether the assay is direct or based on competition. Another application example concerns the detection and/or the quantification of nucleic acids including all operations required for this detection and/or quantification from any specimen containing the target nucleic acids. Among these various operations, reference can be made to lysis, melting, concentration, purification, the steps of enzymatic amplification of nucleic acids, the detection steps incorporating a hybridising step using a DNA chip or a labelled probe, for example. Patent application WO-A-97/02357 or the patent application filed by the applicant under number FR99/00111, clarifies the various steps necessary in the case of nucleic acids.

To this effect, the invention concerns a reaction card consisting of a body, having a front surface and a rear surface defined by an edge, at least one input and at least one output, connected to each other through a network of channels constituting at least one reaction path for at least one fluid, the fluid or fluids being directed inside the card via valves; each valve consists of a flexible film, which can be deformed to allow a fluid to pass through or which cooperates with a compression means to allow the fluid to pass through, the film being fixed on the rear surface of said card at a peripheral indentation of the assembly of channels associated with the valve; the card comprises channels flush with at least one of its surfaces, the channels being of two different cross-sections, a small cross-section for the transfer of fluid or fluids and a large cross-section serving as a reaction compartment; each front or rear surface is bounded by at least one film.

According to a specific embodiment, the body of the card is monobloc and the compression means is affixed and integral with said card, or forms a part of an apparatus allowing the card to be implemented.

According to a specific embodiment, the ratio between the small cross-section and the large cross-section of the channels is between 1:1.01 and 1:10, preferably between 1:1.01 and 1:3.

Still according to a specific embodiment, the channels are flush with all or part of the front surface of the card and the valves are present on the rear surface of said card.

According to yet another specific embodiment, the front surface of the card features a single film at the level of all the channels flush with this surface, and the rear surface of said card features:

- at least a flexible film on the valves,
- at least a hydrophobic filter, and possibly
- at least a film at the level of the channels flush with the rear surface.

According to a specific embodiment, the flexible film(s) form a single film.

According to another specific embodiment, when the card is substantially parallelepiped-shaped, the channels are, totally or in part, circumscribed in the middle part of the card, the blocking filters, which are hydrophobic, are circumscribed on at least one of the sides of said card, and the valves are positioned between the channels and the blocking filters.

In this last embodiment and preferably, the edge includes all of the card's fluid inlets and outlets.

In the case where the card would have a substantially parallelepiped shape, the inlet or inlets are located on one of the sides forming the edge, while the outlet or outlets are located on the other side of this edge.

In this last case and preferably, the inlet or inlets are located on a side opposite the side where the outlet or outlets are located.

In the case where the card is substantially of rectangular parallelepiped shape, the inlet(s) and outlet(s) are located on the two short sides forming the edge.

This invention also concerns the use of a reaction card, as defined above, for testing a biological solution, possibly pre-treated to free ligands; the various biological steps are conducted in the following order:

- capture of ligands,
- recovery of captured ligands in an elution solution,
- mixture of recovered ligands with structural and functional constituents allowing the ligands to be treated, and
- qualitative and/or quantitative detection of treated ligands.

This invention also concerns the use of a reaction card, as defined above, for testing a biological solution, possibly pre-treated in order to free the nucleic acids; various biological steps are carried out in the following order:

- capture of nucleic acids,
- recovery of captured nucleic acids in an elution solution,
- mixture of nucleic acids recovered with the structural and functional constituents allowing amplification of these nucleic acids, and
- qualitative and/or quantitative detection of amplification products.

If necessary, a last step is carried out consisting in analysing these ligands or these amplification products, either in a new location within the card, or after transfer to another apparatus. According to a specific variant of the use, the ligands or nucleic acids captures are subjected to at least a wash solution prior to their recovery.

According to another usage variant, the capture and possible washing operations are conducted N times in succession, N being between 1 and 10.

According to yet another specific usage variant, a treatment of ligands or an amplification of nucleic acids is conducted prior to the transfer to a card compartment or to another apparatus allowing the ligands or the amplicons to be analysed.

Preferably, for all the usage variants described above, the card is used after an apparatus allowing a test solution to be treated, such as an apparatus designed to lyse biological cells and to free the ligands, such as nucleic acids, and before an apparatus designed to analyse the presence of these ligands, such as a DNA chip.

Structurally, the card according to the invention is inserted between two devices which can also be cards, one upstream which pre-treats the test solution, and the other downstream which post-treats the solution already tested.

The accompanying drawings are given by way of example and are not to be taken as limiting in any way. They are designed to make the invention easier to understand.

DEFINITIONS

The term ligand refers to all biological species which can be of nucleic acid or proteic nature, such as an antigen, an antigen fragment, an antibody, an antibody fragment, a hapten, a nucleic acid, a nucleic acid fragment, a vitamin, a peptide or a polypeptide, for example.

A pre-treatment example could consist of a cellular lysis, such as described in the applicant's patent applications:

FR99/04289, filed Apr. 1, 1999, about lysis by sonication,
PCT/FR99/01309, filed under priority Jul. 23, 1998, about mixed magnetic and mechanical lysis,
PCT/FR99/00830, filed under priority Apr. 10, 1998, about electric lysis,
PCT/IB98/01475, filed under priority Sep. 23, 1997, about mechanical lysis.

A post-treatment example, may consist of detection using a biochip. The term biochip refers to all solid support on which ligands are applied, and particularly the term DNA chip refers to all solid support on which nucleic acids are applied. The ligand fixation method can be performed in various ways and notably, for example, through in situ synthesis by photolithographic techniques or by a piezo-electric system, by capillary deposit of preformed ligands. To illustrate this, examples of these biochips applied to DNA chips were given in publications by G. Ramsay, Nature Biotechnology, 16, p40-44, 1998; F. Ginot, Human Mutation, 10, p1-10, 1997; J. Cheng et al, Molecular diagnosis, 1(3), p183-200, 1996; T. Livache et al, Nucleic Acids Research, 22(15), p2915-2921, 1994; J. Cheng et al, Nature Biotechnology, 16, p541-546, 1998 or in patents U.S. Pat. No. 4,981,783 (Augenlicht), U.S. Pat. No. 5,700,637 (Southern), U.S. Pat. No. 5,445,934 (Fodor), U.S. Pat. No. 5,744,305 (Fodor), U.S. Pat. No. 5,807,522 (Brown).

The following definition is to be given to "structural constituents allowing the amplification when they are associated with the functional constituents defined below": nucleotides (desoxyribonucleotides dNTP and/or ribonucleotides NTP), at least one pair of primers which surround specific regions that we wish to amplify, ions ($MgCl_2$, KCl, for example) and a buffer (such as Tris).

The functional constituents are formed by at least one enzyme, preferably two or three enzymes, in the presence of a buffer, such as Tris at pH 7.5, salts and ions allowing the amplification reaction when they are associated with the structural constituents described above.

The term amplicon is used to refer to products of an enzymatic amplification reaction.

Figure 1:
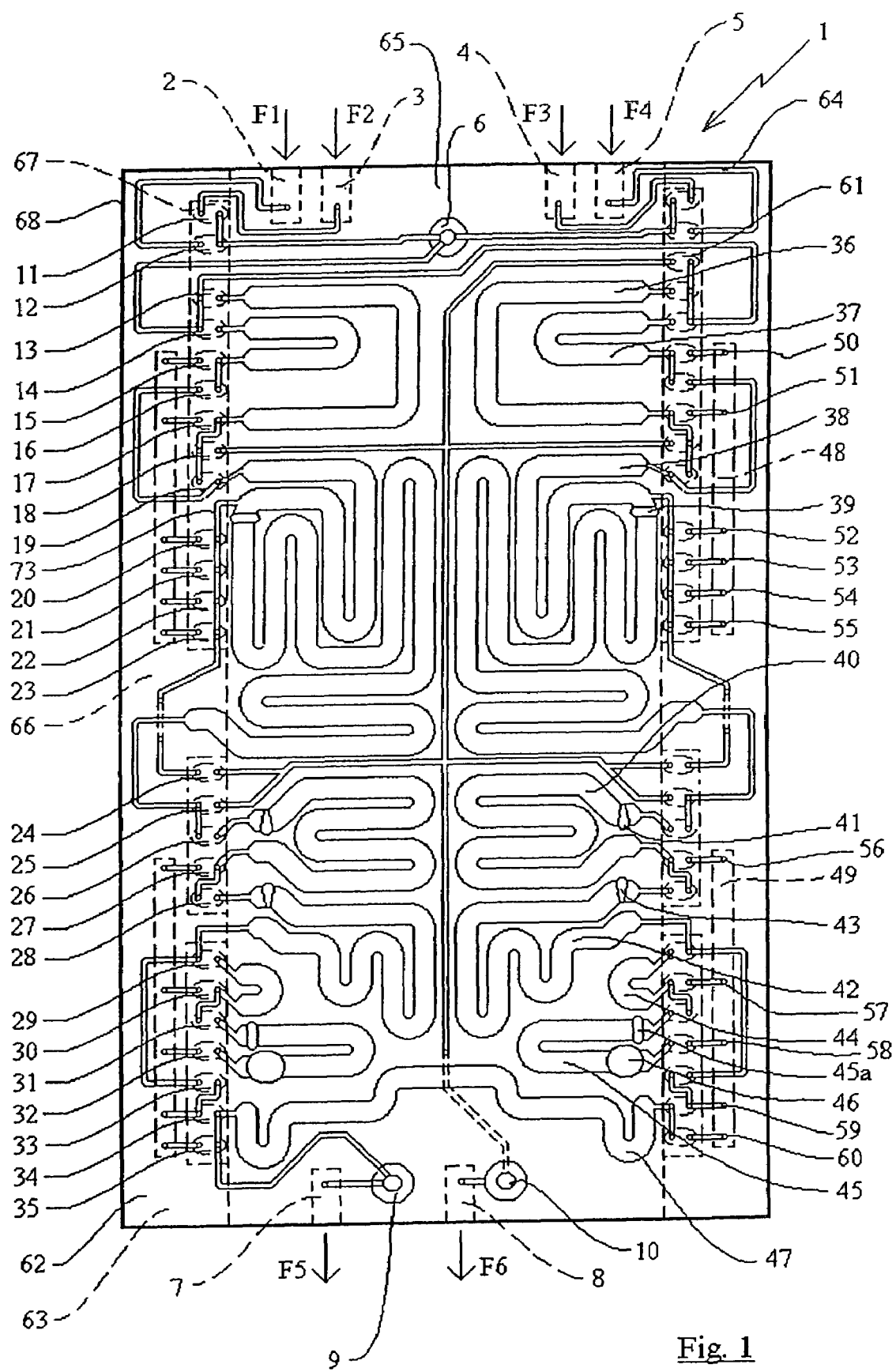
FIG. 1 represents a front view of the reaction card according to a first embodiment of the invention.

Description of the Reaction Card:

The invention concerns a reaction card 1 represented in a first embodiment in FIG. 1. This reaction card 1 consists of a front surface 62 and a rear surface 63 connected by an edge, also referred to as the side 68. All of the elements which form the front surface 62 in this figure are represented in solid lines. In addition, a certain number of through channels 64 can be noted on this surface 62. These channels 64 are partitioned by a transparent film 65, affixed on said front surface 62. Nonetheless, it is not mandatory that this film 65 be transparent, as those which will be described below; it may be opaque, translucent, etc. In addition, the transparent nature allows better viewing of the position of the biological solution being tested 69, or any other solution 70, 71 or 72, introduced into the card 1. The rear surface 63 also features a transparent film 66 which partitions the channels 64, which occasionally are flush with the front 63. These films 65 and 66 consist of BOPP films (Biaxially Oriented PolyPropylen) or other films of the same type, which are soldered or bonded to the body of the card 1, this body being inert in relation to the solutions transferred 69 to 72 or to the reactions undergone.

This film 66 may be present on the entire surface of the card 1, or on certain portions of said card 1. Nonetheless, this film 66 may consist of a partition made of the same material as the rest of the card 1.

It should also be noted that the front 63 is equipped with a certain number of valves, referenced 11 to 35 and also 61 on the figure; these valves 11 to 35 and 61 correspond to the valves described in patent application FR99/08116 filed Jun. 22, 1999 in the name of the applicant. Like this document, all of the valves 11 to 35 and 61 are defined in relation to the outside of the rear surface 63 by a transparent film 67. This film is sufficiently flexible to allow a test solution 69, a treated solution 70, a wash solution 71, or an elution fluid 72, etc. to pass through. It may consist of a silicone membrane or a PE/PET (PolyEthylen/PolyEthylen Tetraphtalate) complex film.

It should be noted that the transparent films 66 and 67 located on the rear surface 63, can be made up of a single transparent film. This would facilitate the fabrication of the card 1. In addition, the transparent film 65 located on the front 62, and the transparent films 66 and 67 located on the rear surface 63, can consist of a single transparent film, which further facilitates the fabrication of such a card which is so equipped.

On this rear surface 63, the presence of several hydrophobic filters 48 and 49 is noted, whose role will be explained below. In fact, in this embodiment of the card in FIG. 1, there are two parallel paths. A left-hand path and a right-hand path which allow the same process to be conducted. Nonetheless, it is quite possible to have only one path or a plurality of paths, that is more than two, according to the number of reactions that one wants to perform.

Finally, on the periphery of the card 1, and more precisely on the two short sides, inlets and outlets can be noted which are separated from one another. Thus, at the top of FIG. 1, four inlets are represented which correspond to four well-defined functions. Thus, if the inlet functions are numbered from left to right, the presence of an inlet 2 for the wash solution 71, an inlet 3 for the test solution 69, an inlet 4 for the elution fluid 72, and finally an inlet for the pressure variation 5 can be noted inside said card 1. All of these inlets 2 to 5 are connected to an inlet ball valve 6 by means of a certain number of channels 64 as well as the first and second valves 11 and 12.

The opposite edge of the card 1 features outlets 7 and 8. The first outlet, outlet 7 for the solution treated 70, is an outlet designed to discharge a predetermined quantity of the solution treated 70 to the outside with a view to subsequent analysis or other subsequent treatment. The second outlet is an outlet for all biological waste and liquids derived from operation of the card 1. The outlet 7 is associated with an outlet ball valve to the outside 9 while the waste outlet is associated with an outlet ball valve for the wastes 10.

Besides the two parts, inlets 2 to 5 in the upper position and outlets 7 and 8 in the lower position, a number of channels, valves and compartments can be noted between these two extreme parts. As already mentioned, the presence of two separate, though identical paths on the left and right of FIG. 1 can be seen. The first compartment, in the upper position and in the shape of an inverted C on the left-hand path and in the shape of a C on the right-hand path, is large and consists of a solution-dosing compartment 36. This compartment 36 contains an elution fluid-dosing compartment 37, which is of similar shape although having a different volume. The ratio between the volume of the solution-dosing compartment 36 and the volume of the elution fluid-dosing compartment 37 is between 1:1 to 10:1, preferably between 1.5:1 to 4:1 and yet more preferably 2:1.

A separation compartment 38 is in underlying position which allows recovery of capture entities, such as magnetic beads, possibly coated with capture oligonucleotides, by adsorption or covalence (refer to patents U.S. Pat. No. 4,672,040 and 5,750,338), and thus, after mixture, the selection by separation of nucleic acids that are to be amplified at a later date. The magnetic beads are inside this separation compartment 38 in the form of a tablet of magnetic beads 39. The applicant, under the following references, describes a particularly interesting embodiment of these magnetic beads in the patent applications filed:

PCT/FR97/00912 under French priority, May 24, 1996, and

PCT/FR99/00011 under French priority, Jan. 6, 1998.

The last of these patent applications concerns thermosensitive magnetic beads, each having a magnetic core covered with an intermediate layer. The intermediate layer is itself covered by a polymer-based outer layer capable of interacting with at least one biological molecule. The outer polymer is thermosensitive and has a predetermined lower critical solution temperature (LCST) between 10 and 100° C. and preferably between 20 and 60° C. This external layer is synthesized from cationic monomers, which generate a polymer capable of binding with the nucleic acids. This intermediate layer isolates the core's magnetic charges, in order to avoid the inhibition problems of the amplification techniques of these nucleic acids. Magnetic beads in the form of tablets have already been described in the prior art, formed by EP-A-0.811.694, for example. The fabrication of tablets in general is also well described in the prior art, for example U.S. Pat. No. 4,678,812 and U.S. Pat. No. 5,275,016. The manufacturing process mentioned above may be used for the synthesis of other tablets which will be disclosed below.

A compartment for recovering structural constituents for subsequent amplification is located in an underlying position. This compartment 40 also contains a tablet 41 consisting of constituents which will allow subsequent amplification. Constituents in the form of tablets, to conduct amplification, have already been described in the prior art. Information can be found in the following documents: the patent U.S. Pat. No. 5,098,893 or the article "Ambient-temperature-stable molecular biology reagents", R. Ramanujam et al., Product Application Focus, Vol. 14, No. 3 (1993), 470-473, for example.

Still in underlying position, an amplification compartment 42 is present which features a tablet 43 containing functional constituents, such as enzymes which, when associated with the structural constituents mentioned previously, will truly lead to an amplification. Enzymes in the form of tablets, to conduct amplification, have already been described in the prior art. Information can be found in the following documents: patent U.S. Pat. No. 4,891,319, WO-A-87/00196, WO-A-95/33488 or the article entitled "Extraordinary stability of enzymes dried in trehalose: simplified molecular biology" by C. Colaco et al., Bio/Technology, Vol. 10, September 1992, 1007-1011.

All amplification techniques can be used. As such, the following nucleic acid amplification techniques exist, among others:

PCR (Polymerase Chain Reaction), as described in patents U.S. Pat. No. 4,683,195, U.S. Pat. No. 4,683,202 and U.S. Pat. No. 4,800,159, LCR (Ligase Chain Reaction), described in patent application EP-A-0.201.184, RCR (Repair Chain Reaction), described in patent application WO-A-90/01069, 3SR (Self Sustained Sequence Replication) with the patent application WO-A90/06995, NASBA (Nucleic Acid Sequence-Based Amplification) with the patent application WO-A-91/02818, SPSR (Single Primer Sequence Replication) with patent U.S. Pat. No. 5,194,370, and TMA (Transcription Mediated Amplification) with patent U.S. Pat. No. 5,399,491.

However, it is possible to perform other steps in the compartment 42 above. For example, these primers could possibly contain a fluorescent marker for the subsequent detection of amplification products, without having to perform an additional step for this labeling. In this manner, such primers are described in the article by D. Whitcombe et al., "Detection of PCR products using self-probing amplicons and fluorescence", Nature Biotechnology (17) 1999, pp804, or in the patent applications GB-A-2.338.301, WO-A-99/29905 and WO-A-99/60157.

An amplification compartment 42 is located below the sampling compartment 44 which will enable the volume of the treated solution 70, present in said amplification compartment 42, to be divided in two. This sampling compartment 44 is designed to receive a predetermined quantity of said treated solution 70. The remaining solution 70 is then being transferred to a convergence compartment 47 located in the lower position of said card 1, but in upper position in relation to the fluid outlet means which are associated with treated solution 70 or the wastes. The convergence compartment 47 thus contains a single solution containing all the amplified solutions that must either undergo other treatments within the same card, or be transferred to another apparatus for analysis. This single solution comes from all of the paths, which make up the card 1, that is in this case, the left-hand path and the right-hand path.

When the amplification products contained in the convergence compartment 47 are transferred to another apparatus for analysis, the transfer can be carried out via a tube, as described in FIGS. 8 to 11 of patent request PCT/FR99/02137 filed Sep. 8, 1999 by the applicant. This other apparatus may consist of a support featuring, on one of its sides for example, high density capture probes, DNA chips for example, developed by the Affymetrix Company ("Accessing Genetic Information with High-Density DNA arrays", M. Shee et al., Science, 274, 610-614. "Light-generated oligonucleotide arrays for rapid DNA sequence analysis", A. Caviani Pease et al., Proc. Natl. Acad. Sci. USA, 1994, 91, 5022-5026), or any other chip system containing nucleic acids fixed on a solid support, such as the DNA chips defined above.

The aliquot present in the sampling compartment 44 will then be transferred to a detection and reading compartment 45. This compartment 45 features a tablet which contains detection means 45a. Based on the prior art documents mentioned above, it is possible to manufacture, for example, tablets 45a containing labelled nucleic acids complementary of all or part of the amplicons which must be obtained during the previous steps.

As described previously, it is also possible to perform the labeling step during amplification by means of labelled primers. In this case, a tablet 45a is not needed, and the compartment 45 is thus simply a reading compartment.

This labeling and reading compartment 45 thus features a marker tablet 45a at its inlet and a reading cell 46 downstream. This reading cell 46 allows detecting if amplification has been successful, by fluorescence measurement for example. If so, this allows the technician or the programmable apparatus, which uses such a card 1, to determine if there is need to transfer the treated solution 70, present in the convergence compartment 47 to amplified sequence analysis means, these means being able to be integrated into the card 1 or contained in another apparatus more specifically designed for this function.

The movement of fluids within the card 1, whether it be the test solution 69, the solution treated 70, the wash solution 71 or the elution fluid 72, are produced through hydrophobic filters which are located downstream from certain valves. Each hydrophobic film 48 or 49 features a number of blocking filters, referenced 50 to 55 for the film 48 or 56 to 60 for the film 49. Their use will be described below.

Figure 15:
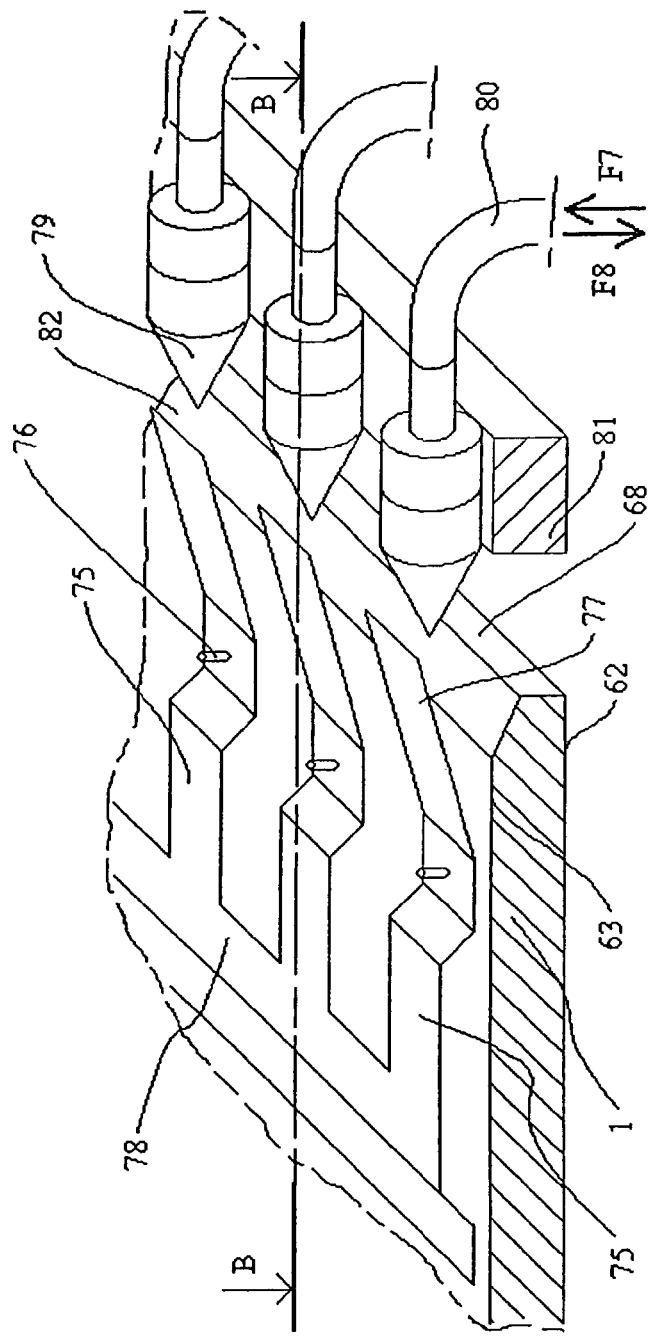
FIG. 15 represents a perspective view of several valves associated with the reaction card.
Figure 16:
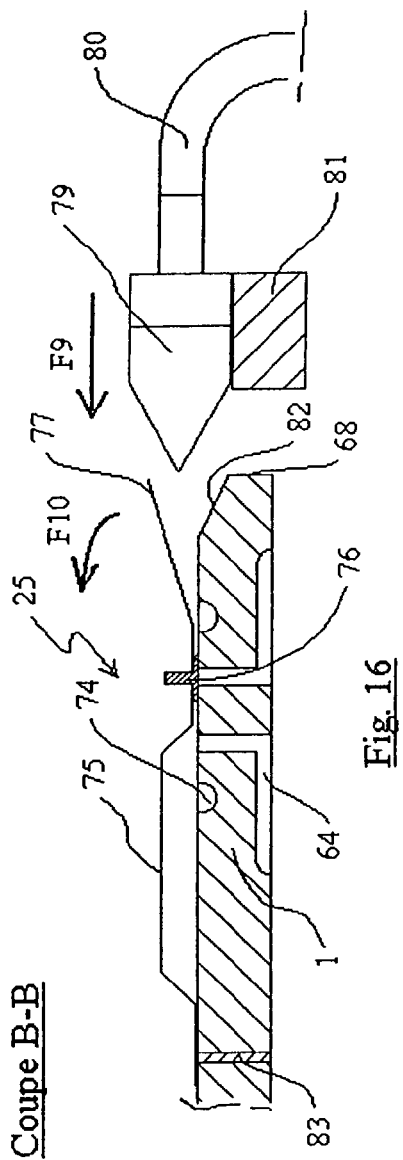
FIG. 16 represents a cross-sectional view along B-B of FIG. 15.

Description of the Valves:

As described in patent application FR99/08116, filed in 1999 by the applicant, valves 11 to 35 and 61 have a structure which address the problems of welding films onto a solid support, such as the body of a reaction card 1, generally consisting of plastic materials. This invention offers a particularly interesting application in the card 1 according to the invention, as the body of said card 1 features a peripheral groove or reinforcement 74, clearly shown in FIG. 16, which will receive a flexible transparent film 67 in the zone circumscribed, said films 67, of which there are four in FIG. 1, and the body of the card 1 being integral to one another by a weld 84 located in the bottom of the groove 74. As a result, the weld causes no deformation of the upper surface of the card 1 and thus no subsequent problem for using said card 1 and performing assays. The manipulation of electromagnets or actuators of adapted size, as represented in FIGS. 15 and 16, can be used to control these valves 11 to 35 and/or 61.

Card Operation:

In the following description, the reference made to valves 11 to 35 and 61 will concern only valves 11 to 35 of the left-hand path, in the case where the path concerned is not mentioned. All information concerning valves 11 to 35 and 61 of the right-hand path will have their position on this right-hand path specified. In addition, it should be pointed out that when a valve 11 to 35 is closed, it is either the left-hand orifice, referred to as the outside orifice, or the right-hand orifice, referred to as the inside orifice, of said valve 11 to 35 which is plugged. This is also true for the right-hand path and for valves 11 to 35 and 61, although the position is reversed. Thus, the right-hand orifice is referred to as the outside orifice, and the left-hand orifice is referred to as the inner orifice, of said valve 11 to 35 or 61.

Finally, the valves 11 to 35 and 61 are normally at rest in open position. During the transfer of fluid, liquid or gas, the closed valves direct this fluid.

1$^{st}$ Step—Dosing of the Test Solution:

In this first step, the operation of all the components will be described in detail. While subsequent steps will not be described with the same detail level, the main functions will be the same, and information will be easy to extrapolate.

Figure 2:
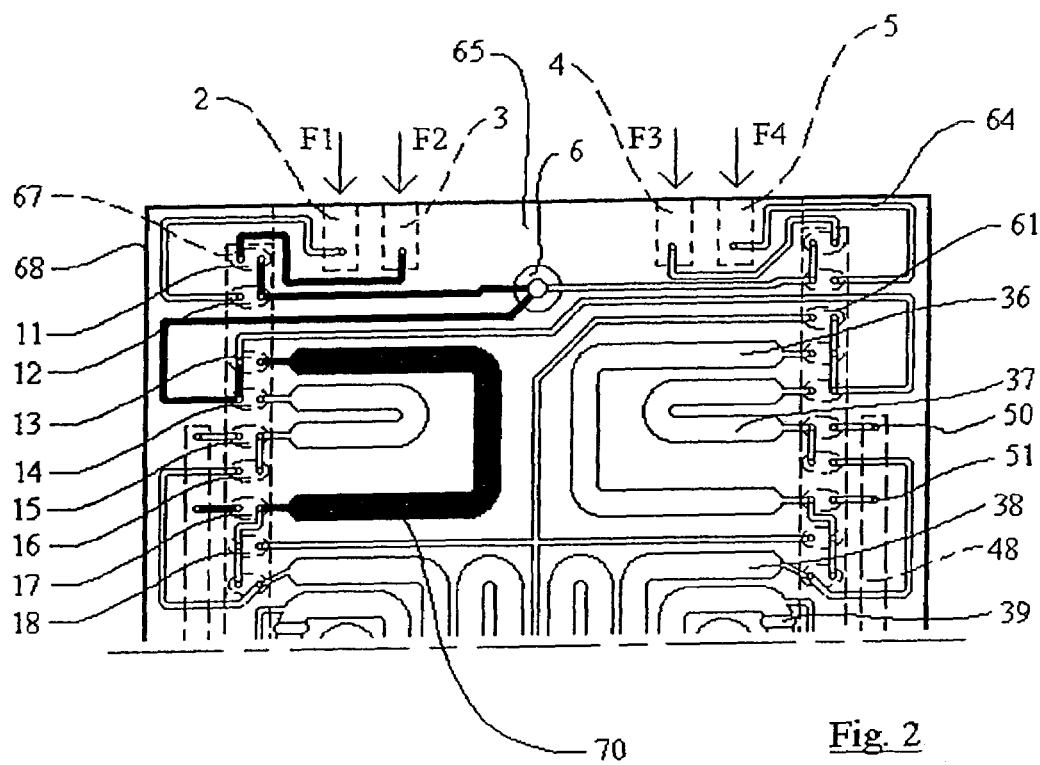
FIG. 2 represents an identical although partial view of FIG. 1, when the card's operating process is underway, said card having received the test solution.

The test solution 69 is introduced into the card 1 via the inlet 3, along F2. The solution 69 follows the channel 64 between the inlet 3 and the first valve 11, which is open. Owing to this, said solution 69 can flow to the second valve 12 whose outside orifice is closed, which prevents this solution 69 from entering the channel 64 which returns to the inlet 2 and directs said solution 70 to the ball valve of inlet 6 which is open. Two channels 64 leave this ball valve 6, one toward the left-hand path and the other toward the right-hand path. The channel leading to the right-hand path is plugged by the closure of the inner orifice of the second valve 12 of the right-hand path. The channel leading to the left-hand path allows the test solution 69 to pass through, as the third valve 13 and the seventh valve 17 are open. The objective is to allow the dosing compartment 36 to be filled with said solution 69 according to FIG. 2. For this reason, the inside valve of the forth valve 14 and the outside orifice of the eighth valve 18 are closed, as is the case of the outside valve of the fourth valve 14 of the right-hand path.

If one wants to also fill the dosing compartment 36 with the test solution 69 from the right-hand path, the inside orifice of the forth valve 14 of the right-hand path must be closed, which leaves the outside orifice of this valve 14 open so that the compartment 36 can be filled, while that of the dosing compartment 37 of the elution liquid 72 is not possible. The outside orifice of the intermediary valve 61 and the outside orifice of the intermediate valve 61 and the outside orifice of the eighth valve 18 of the right-hand path must be closed.

Now returning to the single filling of compartment 36 of the left-hand path, the test solution 69 will be able to fill all the channels 64 from the inlet 3 to the blocking filter 51 of said solution 69. This blocking filter 51 is placed in the continuation of the outside orifice of the seventh valve 17. It consists of a first hydrophobic filter 48, which allows gaseous, but not liquid, fluids to pass through. An interesting material is used to make this filter: the VERSAPOR 200R membrane manufactured by the American company GELMAN SCIENCES (USA). It is the configuration of FIG. 2. When this type of filter has been used once, it cannot be reused a second time.

Finally, in order to accurately meter the volume of solution 69 in the dosing compartment 36, the volume of which is 100 μl, the channels 64 must be purged. To do this, a wash solution 71 is introduced via the inlet 2 along F1. In this case, the following valves are closed:

the inside orifice of the first valve 11,
the inside orifice of the third valve 13,
the inside orifice of the fourth valve 14,
the inside orifice of the eighth valve 18,
the inside orifice of the fourteenth valve 24,
the inside orifice of the fifteenth valve 25,
the inside orifice of the second valve 12 of the right-hand path,
the inside orifice of the third valve 13 of the right-hand path,
the inside orifice of the fourth valve 14 of the right-hand path,
the inside orifice of the eighth valve 18 of the right-hand path,
the inside orifice of the fourteenth valve 24 of the right-hand path,
the inside orifice of the fifteenth valve 25 of the right-hand path, Once the washing operation is finished, the wash solution 71 present in the channels 64 is replaced by an inert gas, air for example. In this case, air is injected under pressure by the inlet 5 along F4. The closed valves are thus indicated, except for the following characteristics:

reopening of the inside orifice of the first valve 11,
closure of the inside orifice of the second valve 12,
closure of the inside orifice of the first valve 11 of the right-hand path, and
reopening of the inside orifice of the second valve 12 of the right-hand path.

Figure 3:
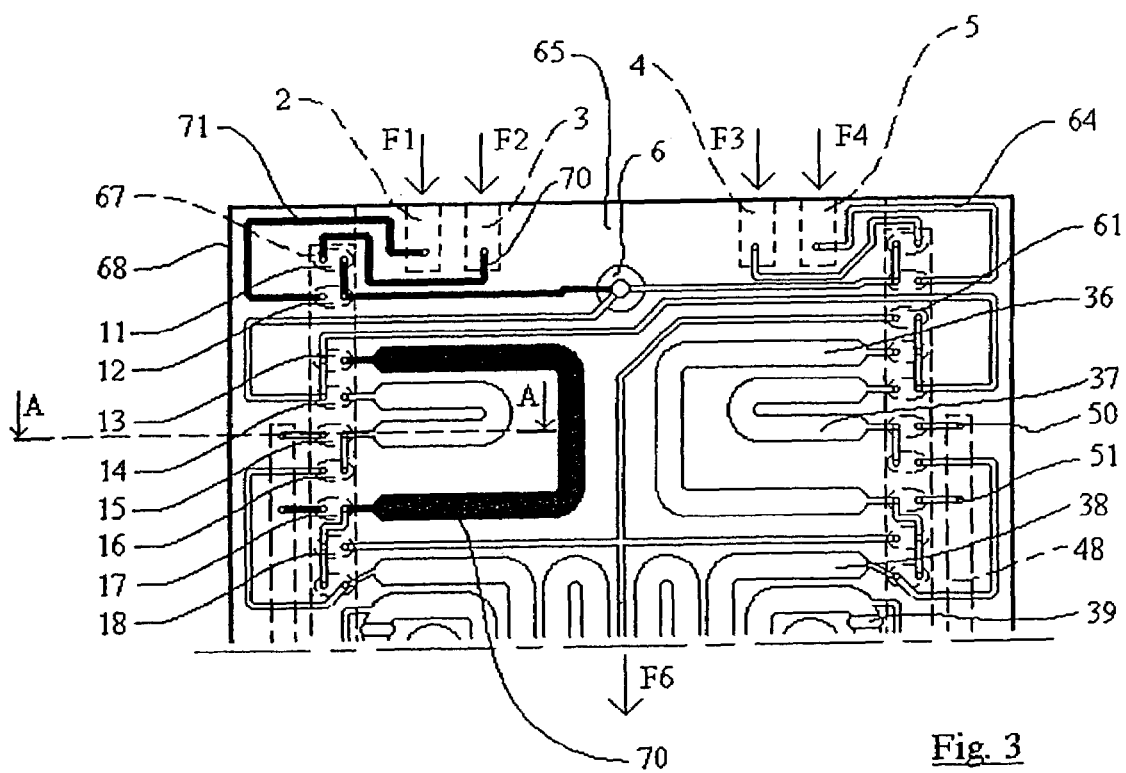
FIG. 3 represents a view identical to FIG. 2, when the card's operating process is underway, said card having undergone a purge allowing the volume of the test solution to be precisely metered.

In this configuration, the result obtained is that represented in FIG. 3. The test solution 69, which was present at the level of the channels 64, was thus discharged by the waste outlet 8 along F6. In addition, the channels 64 are clean. Only the length of channel 64 between the inlet 2 and the inner orifice of the second valve 12 contains wash solution 71, which can be used at a later time. Of course, the ball valves of inlet 6 and the waste outlet 10 must be open.

This washing operation can, of course, be repeated several times. However, this result can be obtained by not performing the washing operation. In this case, the remaining solution 69 located in the channels 64 only has to be pushed via the air inlet 5 along F4. The result will be identical except there will be no wash solution 71 between the inlet 2 and the outside orifice of the second valve 12, and the wash solution 71 present between the inside orifice and the second valve 12 and the ball valve of inlet 6 will be replaced by the test solution 69. This possibility is thus less interesting, even if its possible, as solution 69 likely to pass the ball valve 6 remains in the card 1 as soon as wash solution 71 is introduced along F1.

In both cases proposed, the nucleic acids in this compartment 36 can be denatured. To do this, it is heated to a temperature between 80 and 100° C.

$2^{nd}$ Step—Separation of the Nucleic Acids Contained in the Test Solution:

In this second step, the test solution 69, which has just been dosed and is present in the compartment 36, is transferred in the following compartment, referred to as the separation compartment 38. The test solution 69 located in compartment 36 is thus pushed toward the separation compartment 38, by the introduction of an inert fluid into the channel network 64 via the input 5 along F4. In this case, the following valves are closed:

the inside orifice of the second valve 12,
the inside orifice of the fourth valve 14,
one of the orifices of the sixth valve 16,
the inside orifice of the eighth valve 18,
the inside orifice of the eleventh valve 21,
the outside orifice of the fifteenth valve 25,
the inside orifice of the first valve 11 of the right-hand path,
the outside orifice of the fourth valve 14 of the right-hand path, For informational purposes, the closing of a valve cannot be mandatory, if the closure of another upstream or downstream valve has the same effect. In this manner, the sixth valve 16 can remain open. In this case, the inside orifice of the fifth valve 15 should be closed.

Figure 4:
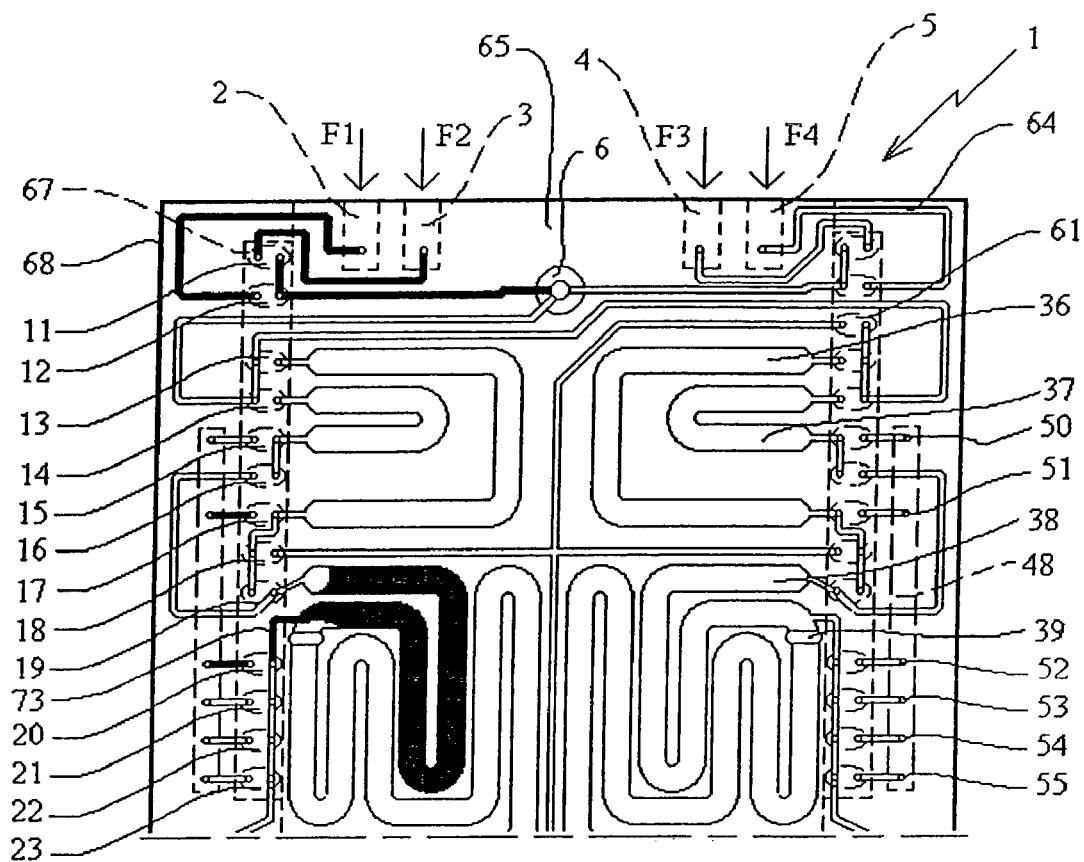
FIG. 4 represents an identical although partial view of FIG. 1, when the card's operating process is underway, the test solution being transferred from the solution's dosing compartment to the part upstream from the separation compartment.

The transfer of the dosed solution 69 is obtained as clearly represented in FIG. 4 and is made possible by the presence in relation with this compartment 38 with a blocking filter 52 which is connected to a branch connection 73 in intermediate position along said compartment 38. This filter 52 being associated with the tenth valve 20, the air downstream of said solution 69 can escape via this blocking filter 52. When the solution 69 reaches the blocking filter 52, via the branch connection 73, the progress of said solution 69 is stopped. Furthermore, the total volume of this solution 69 is less than the volume of said compartment 38 upstream from said branch connection 73 and shall thus be circumscribed in this upstream part of the compartment 38.

It should be noted that in this position, the dosed solution 69 has not yet reached the magnetic bead tablet 39, which is itself located downstream from the branch connection.

In this position, the volume of air downstream from said test solution 69 is trapped but remains a significant volume. It is then possible, by forcing the air inlet along F4, to compress the trapped air. When several to-and-fro movements are made, the solution 69 will dissolve the magnetic bead tablets 39. These beads will be present in a homogenous manner in this new solution 70, referred to as the treated solution 70, a name which it will be assigned afterwards regardless of its level or treatment (magnetic beads, structural constituents, functional constituents, amplicons) as soon as the base liquid used is the test solution 69. In addition, for the wash solution 71 which will be described below, when this wash solution 71 has fulfilled its function and contains waste that must be discharged, its reference is not modified. Furthermore, for the elution solution 72 which will also be described below, when the elution liquid 72 recovers the structural constituents, amplicons or others, this liquid is thus referred to as a treated liquid 70.

The to-and-fro movement described above, and which will be explained in association with the wash solution 71 and elution liquid 72 below, is possible owing to the configuration of the separation compartment 38. Thus, this compartment 38 has a greater volume that the volume of test liquid 69 introduced, such that the liquid 69 circumscribes downstream a volume of air which is captured. Owing to this fact, when said liquid 69 is pushed by an increase in upstream pressure, either by a thrust due to said liquid 69 itself, or by an increase in the air pressure by the introduction of a surplus gas at inlet 5, and when this thrust is then released, the magnetic bead tablet 39 can be driven by a to-and fro movement. This movement thus optimises the placement or replacement of said magnetic beads into suspension.

In this respect, the ratio that exists between the volume of the compartment 38 upstream of the branch connection 73 and the volume of said compartment 38 downstream from said branch connection 73 is between 1:2 and 1:5, and preferably is 1:3. The ratio between the volume of said solution 70 and the volume of the compartment 38 downstream of this solution 70 is thus substantially equal or less. For example, in the case where this ratio is less, it is between 1:2.5 and 1:6, and preferably it is 1:3.5. Owing to the ratios mentioned above, in the example described on the figures, the total volume of the dosing compartment 36 being 50 µl, the separation compartment 38 is thus 150 µl.

The magnetic beads have the property of binding specifically nucleic acids. To this end, the test solution mixture 69 and the magnetic bead tablets 39 must be subjected to a temperature or a temperature cycle between 25 and 60° C. Then, magnetic separation of the beads is conducted against at least one of these transparent films 65 and/or 66 which partitions the card on its front surface 62 and/or rear surface 63, at the level of its separation compartment. The magnetic separation of the magnetic beads takes place before the treated solution 70 is discharged along F6.

If required, these treated solution 70 dosing steps and the separation of nucleic acids can be repeated N times, N being between 1 and 10, in order to treat the volumes of treated solution 70 greater to the volume of the separation compartment 38.

The magnetic beads are then washed so that only the nucleic acids sought are retained. When the wash solution 71 is introduced along F1, by the inlet 2, the following valves are closed:

one of the orifices of the first valve 11,
the inside orifice of the fourth valve 14,
one of the orifices of the sixth valve 16,
the inside orifice of the eighth valve 18,
the inside orifice of the twelfth valve 22,
one of the orifices of the sixteenth valve 26, one of the orifices of the additional valve 61 of the right-hand path, the inside orifice of the second valve 12 of the right-hand path, and the outside orifice of the fourth valve 14 of the right-hand path.

The wash solution 71 will thus flow into the separation compartment 38, where the magnetic beads are still magnetized. The blocking filter 53 stops this liquid, then the magnetic separation is interrupted and a to-and-fro movement is performed so that said wash solution 71 can properly wash the nucleic acid-carrying magnetic beads.

The magnetic separation of magnetic beads is again implemented before the wash solution 71 is discharged along F6. The closed valves are, of course, identical to those used during the discharge of the remaining test solution 70, the nucleic acids of which were captured by the magnetic beads.

When the wash solution is reintroduced along F5 to perform a second washing operation, the same valves as for the first washing operation are closed, except for the inside orifice of the second valve 22 that is open while the inside orifice of the thirteenth valve 23 is closed. In this configuration, the new wash solution 71 introduced is stopped by the blocking filter 54, connected to the twelfth valve 22. Magnetic separation is interrupted and a to-and-fro movement is conducted so that said liquid 71 can best clean the nucleic acid-carrying magnetic beads.

Once the washing operation is finished, the wash solution 71 present in the channels 64 is replaced by an inert gas, air for example. In this case, air is injected under pressure by the inlet 5 along F4. The discharged wash solution 71 exits the card 1 via the outlet 8 along F6 through the waste outlet ball valve 10. The closed valves are thus indicated, except for the following characteristics:

reopening the inside orifice of the first valve 11, closure of the inside orifice of the second valve 12, closure of the inside orifice of the first valve 11 of the right-hand path, and reopening of the inside orifice of the second valve 12 of the right-hand path.

Of course, this step can be conducted between the two washing steps.

This step can be repeated several times, of course, the dirty wash solution 71 always being discharged via the outlet 8, via the outlet ball valve 10, along F6. In this case, other blocking filters must be provided between blocking filters 54 and 55.

3$^{rd}$ Step—Recovery of Magnetic Beads by the Elution Liquid:

In this third step, the test solution 70 was almost completely discharged along F6. Only the nucleic acids, which were captured during the previous step, remain attached to the magnetic beads. These magnetic beads are still present as magnetic separation is again conducted while waiting for the recovery of nucleic acids by an elution liquid 72, which is the purpose of this step.

Initially, the elution liquid 72 to be used must be correctly dosed. The volume required in this case is 50 µl. There is thus a ratio of 1:2 between the volume of the treated solution 70 and the volume of the elution liquid 72. Nonetheless, a ratio varying between 1:1 and 1:10 is possible. Due to the fact that this step can be repeated 1 to 10 times, this ratio may thus range from 1 to 100. The volume of elution liquid 72 is dosed in the dosing compartment 37.

To do this, the elution liquid 72 is introduced via the inlet 4, along F3. Said liquid 72 then follows the channels 64 to fill the dosing compartment 37. The liquid 72 is stopped by the blocking filter 50.

The following valves are closed:

the inside orifice of the second valve 12, the outside orifice of the third valve 13, the inside orifice of the sixth valve 16, and the outside orifice of the second valve 12 of the right-hand path.

Figure 5:
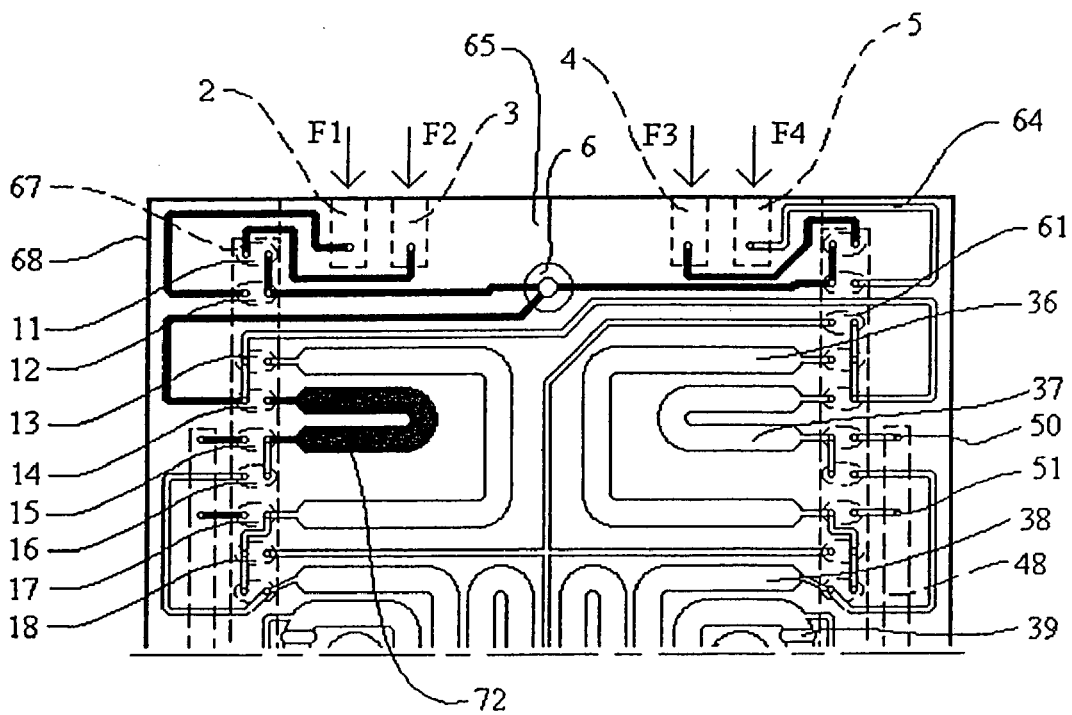
FIG. 5 represents a view identical to FIGS. 2 and 3, when the card's operating process is underway, said card having received the elution solution.

This configuration is clearly represented in FIG. 5.

Figure 6:
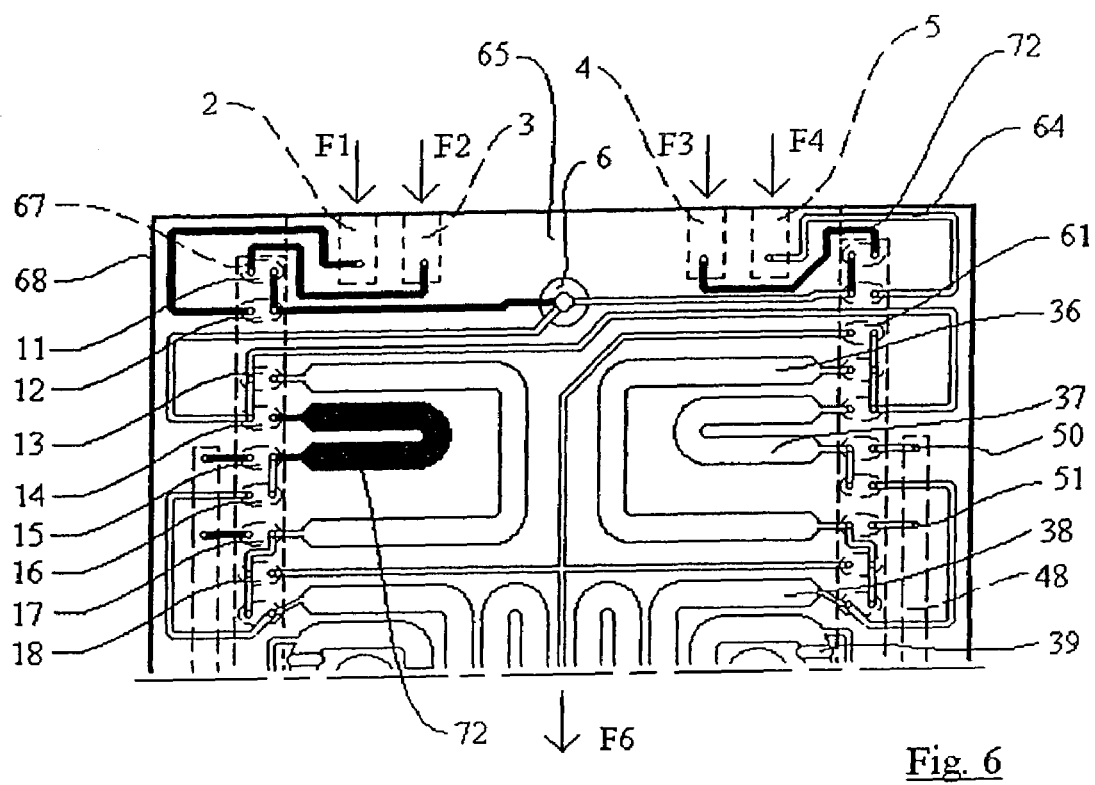
FIG. 6 represents a view identical to FIG. 2, 3 and 5 when the card's operating process is underway, said card having undergone a purge allowing the volume of elution fluid to be precisely metered.

Once the elution liquid 72 dosing operation is finished, it is replaced in the channels 64 by an inert gaseous fluid, air for example. In this case, air is injected under pressure by the inlet 5 along F4. The discharged elution liquid 72 exits the card 1 via the outlet 8 along F6 through the waste outlet ball valve 10. A card 1 is thus obtained which has a liquid distribution as represented in FIG. 6. The following valves are closed:

closure of one of the orifices of the first valve 11, reopening of the outside orifice of the second valve 12, closure of the inside orifice of the eighth valve 18, closure of the inside orifice of the fourteenth valve 24, closure of the inside orifice of the fifteenth valve 25, reopening of the outside orifice but closure of the inside orifice of the third valve 13, closure of the inside orifice of the third valve 13 of the right-hand path, closure of the inside orifice of the fourth valve 14 of the right-hand path, closure of the inside orifice of the eighth valve 18 of the right-hand path, closure of the inside orifice of the fourteenth valve 24 of the right-hand path, and closure of the inside orifice of the fifteenth valve 25 of the right-hand path.

The elution liquid 72, which has just been dosed and is present in the compartment 37, is transferred to the following compartment, referred to as the separation compartment 38. Said liquid 72 located in compartment 36 is thus pushed toward the separation compartment 38, by the introduction of an inert fluid into the channel network 64 via the input 5 along F4. The elution liquid 72 is stopped when said liquid 72 reaches the blocking filter 55. In this case, the following valves are closed:

the inside orifice of the second valve 12, the outside orifice of the third valve 13, the outside orifice of the ninth valve 19, one of the orifices of the fourteenth valve 24, the outside orifice of the fifteenth valve 25, and the inside orifice of the first valve 11 of the right-hand path.

Figure 7:
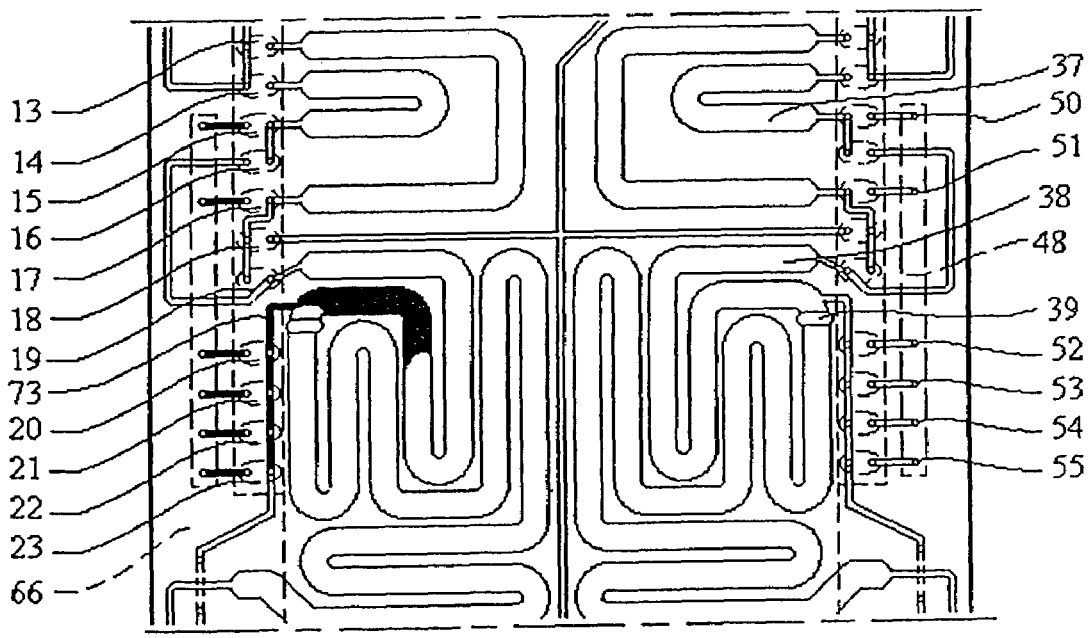
FIG. 7 represents an identical although partial view of FIG. 1, when the card's operating process is underway, the elution fluid being in the separation chamber and allowing nucleic acids to be recovered.

The configuration of the card 1 after displacement of the elution liquid 72 is represented in FIG. 7. In this position, said elution liquid 72 allows the magnetic beads associated with the nucleic acids to be recovered. At this stage, it is possible to perform a mixing operation as indicated above with the test solution 70 and the magnetic beads of the tablet 39.

The elution liquid 72, which may be a buffer such as Tris at pH 7.5 and with weak ionic strength, will enable the nucleic acids of the magnetic beads to be separated, by performing an incubation at a temperature between 25 and 60° C. Magnetic separation of the magnetic beads alone is then conducted, the nucleic acids being in suspension in said liquid 72.

Figure 8:
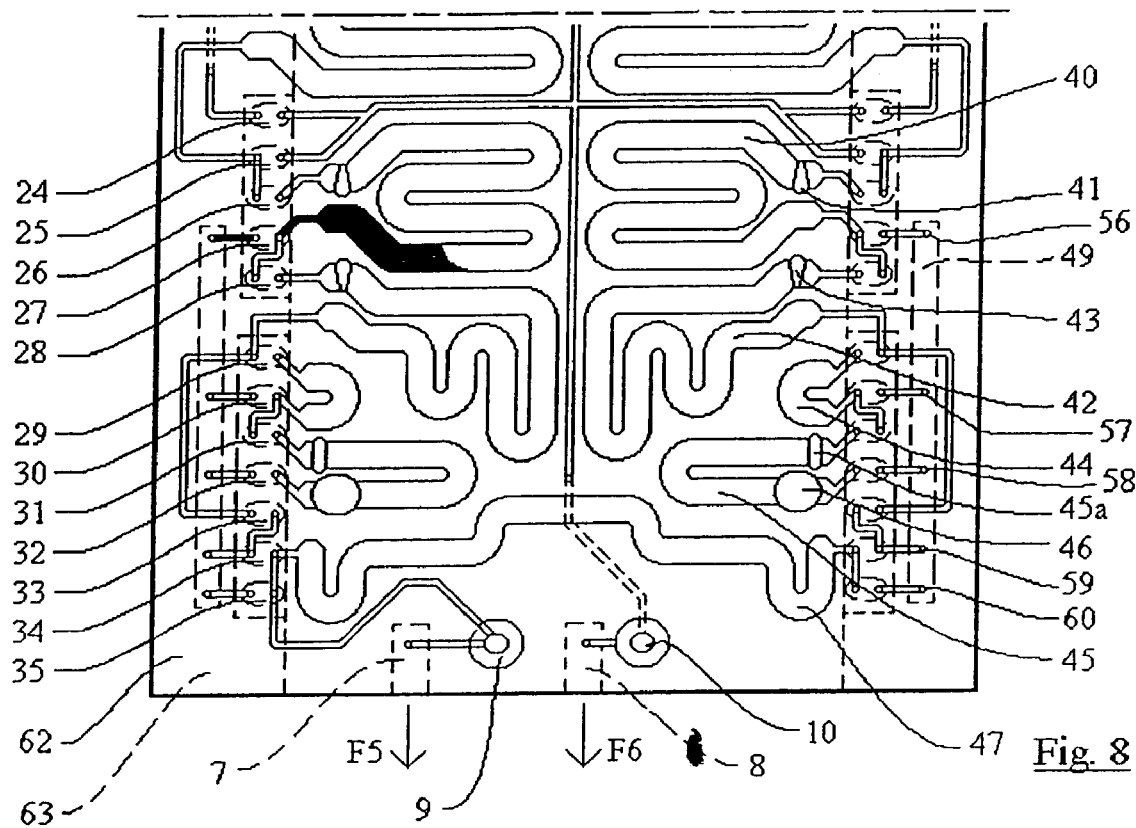
FIG. 8 represents an identical although partial view of FIG. 1, when the card's operating process is underway, the elution fluid, which contains nucleic acids, being transferred into the structural component recovery compartment allowing amplification to take place.

4th Step—Transfer if the Elution Liquid and Recovery of Structural Constituents of the Amplification:

This fourth step is represented in FIG. 8. The following valves are closed:
- the inside orifice of the second valve 12,
- the outside orifice of the third valve 13,
- the outside orifice of the ninth valve 19,
- one of the orifices of the fourteenth valve 24,
- the inside orifice of the fifteenth valve 25,
- the outside orifice of the eighteenth valve 28, and
- the inside orifice of the first valve 11 of the right-hand path.

In this configuration, the elution liquid 72 containing the nucleic acids extracted from the test solution 70 is transferred from the separation compartment 38 to the constituent recovery compartment 40 enabling amplification. This concerns structural constituents that allow this amplification to take place. These constituents are amalgamated and form a tablet 41 located at the entrance of the compartment 40, such that the elution liquid will rapidly dissolve the tablet 41 when it enters this compartment 40 and will carry the constituents with it to its position as described in FIG. 8.

The volume of this compartment 40 is 150 µl, that is with a ratio of 1:3 with the 50 µl of the elution liquid 72. Nonetheless, this ratio can be 1:2 to 1:5. This ratio allows the displacement of said liquid 72 containing the nucleic acids and loaded with structural constituents, which facilitates mixing.

The transfer is made through the increase in the pressure inside the card 1 upstream from the elution liquid 72. This pressure increase is made by injecting air or any other inert gaseous fluid via inlet 5, along F4.

The liquid 72, containing nucleic acids and containing structural constituents of the amplification, will be stopped by the blocking filter 56 associated with the seventeenth valve 27.

During this step, the inner orifice of the sixteenth valve 26 and the inner orifice of the seventeenth valve 27 are closed when said liquid 72 is in this compartment 40. Incubation in performed for 1 to 15 minutes at a temperature between 30 and 65° C., which allows the primers to become attached to the corresponding nucleic acids. Then, the temperature is adjusted to a value between 37 and 42° C. As described above, the liquid derived from this 4th step, which essentially contains the elution liquid 72 and the structural constituents likely to allow amplification in certain conditions, is called solution or treated liquid 70.

Figure 9:
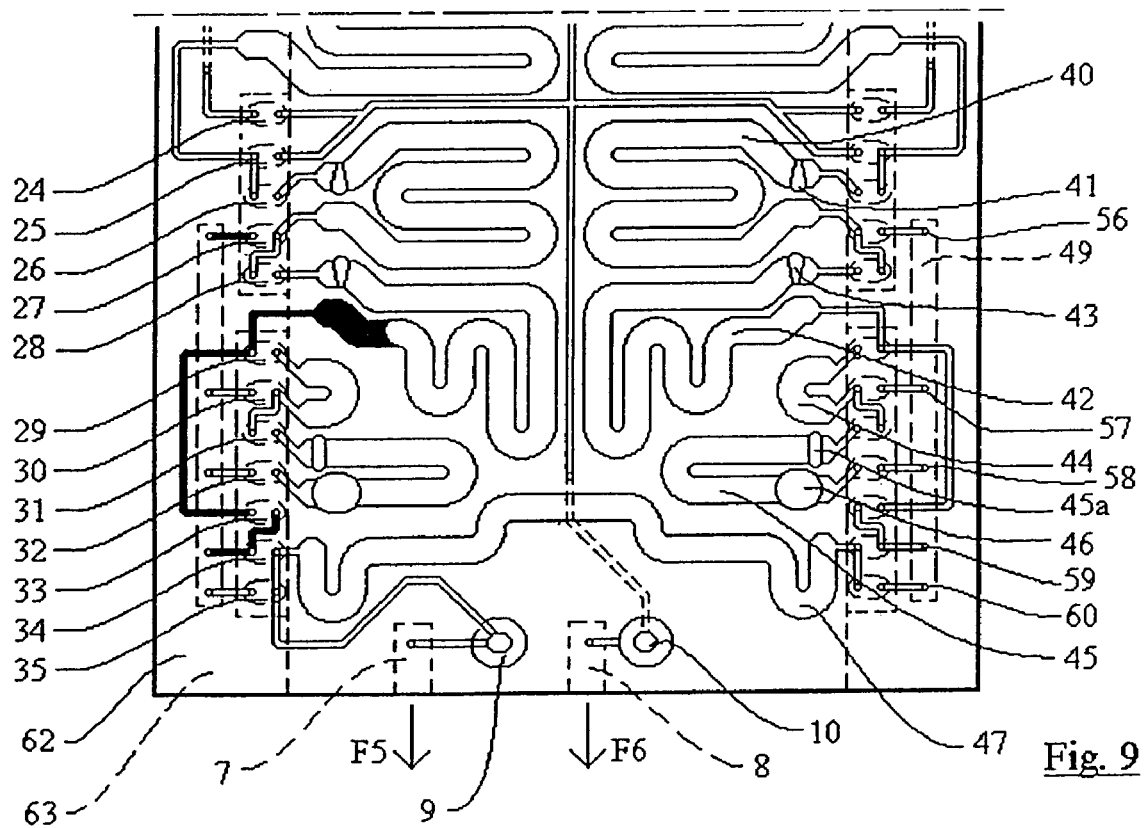
FIG. 9 represents a view identical to FIG. 8, the elution fluid, which contains nucleic acids and the structural constituents, being transferred into the functional constituent recover compartment allowing amplification to take place.

5th Step—Transfer of the Treated Liquid and Recovery of the Functional Constituents of the Amplification:

This fifth step is represented in FIG. 9. The following valves are closed:
- the inside orifice of the second valve 12,
- the outside orifice of the third valve 13,
- the inside orifice of the ninth valve 19,
- the inside orifice of at least one of the valves 20, 21, 22 and/or 23 and/or one of the orifices of the fourteenth valve 24,
- the inside orifice of the fifteen valve 25,
- the inside orifice of the twenty-fourth valve 34, and
- the inside orifice of the first valve 11 of the right-hand path.

In this configuration, the elution liquid 72, containing the nucleic acids and the structural constituents likely to allow amplification, referred to as the treated solution 70, is transferred from the structural constituent recovery compartment 40 allowing amplification to the functional constituent recovery compartment 42 enabling this same amplification to take place. The blocking filter 59 stops the movement of said treated solution 70.

These functional constituents essentially contain enzymes allowing the amplification operation to be carried out. The type and number of these enzymes and other constituents is a function of the amplification technique chosen. These constituents are amalgamated and form a tablet 43 located at the entrance of the compartment 42, such that the solution treated will rapidly dissolve the tablet 43 when it enters this compartment 42 and will carry the constituents with it to its position as described in FIG. 9. This position is only a momentary intermediate position as the pressure along F4 will allow for the subsequent transfer of the elution liquid 72 containing the structural and functional constituents allowing amplification to be performed, according to, of course, another valve configuration.

The transfer is identical to that of the fourth step. It is thus carried out by increasing the pressure inside the card 1 upstream from the treated liquid 70. Injecting air or any other inert gaseous fluid via inlet 5, along F4, makes this pressure increase. There is also the same ration of 1:3 between the liquid volume 70 and the volume of the compartment 42, with the same to-and-fro mixing effect already described above.

During this step, the inside orifice of the eighteenth valve 28 and the inside orifice of the nineteenth valve 29 are closed when said liquid 70 is in this compartment 42. Heating takes place for 30 to 90 minutes at a temperature between 30 and 75° C., preferably between 37 and 42° C., if isothermal amplification is desired, using such techniques as NASBA, TMA, 3SR, SBA. To perform a PCR, the temperatures must be changed several time while remaining within the 30 to 100° C. temperature range, in order to do several successive amplification cycles.

It should be noted that the fourth and fifth steps can be combined to form a single step. The only condition is to use stable enzymes at a temperature greater than or equal to 50° C., referred to as thermostable enzymes.

Figure 10:
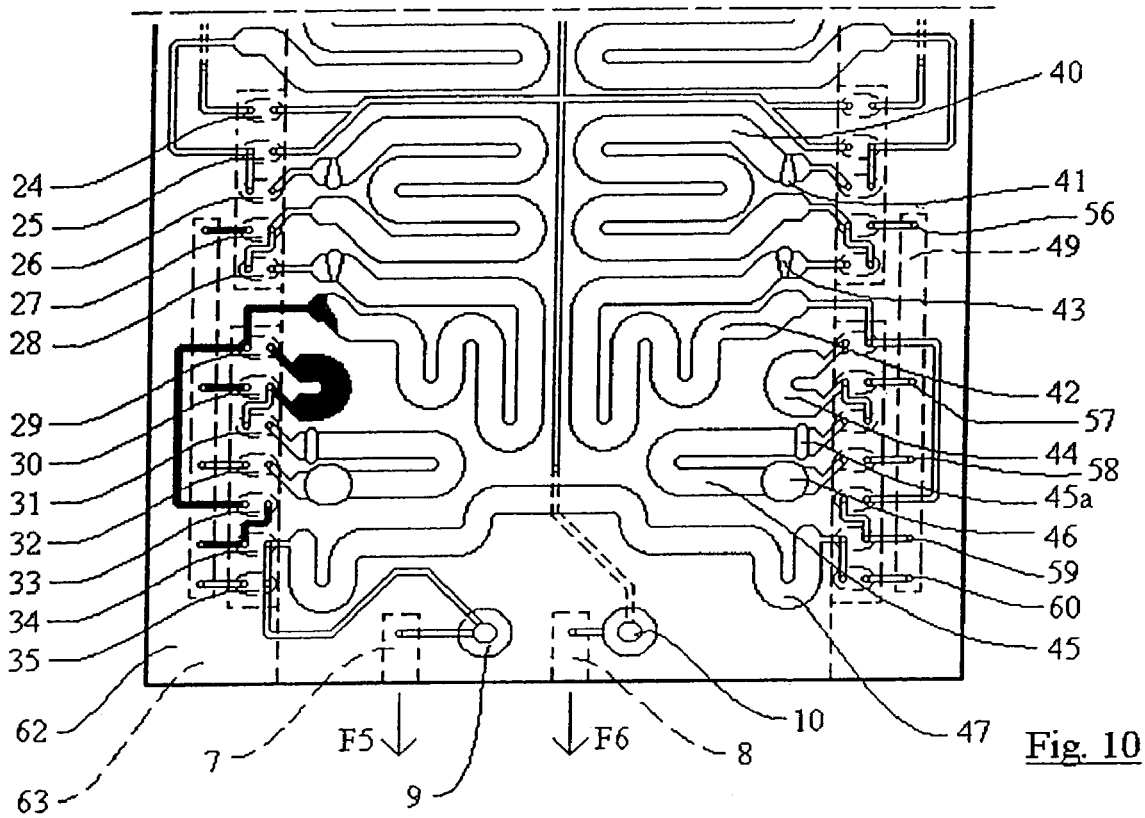
FIG. 10 represents a view identical to FIGS. 8 and 9, the elution fluid, which contains the nucleic acids and the functional and structural constituents, being partly transferred into the sampling compartment in view of the step represented in FIG. 12.
Figure 11:
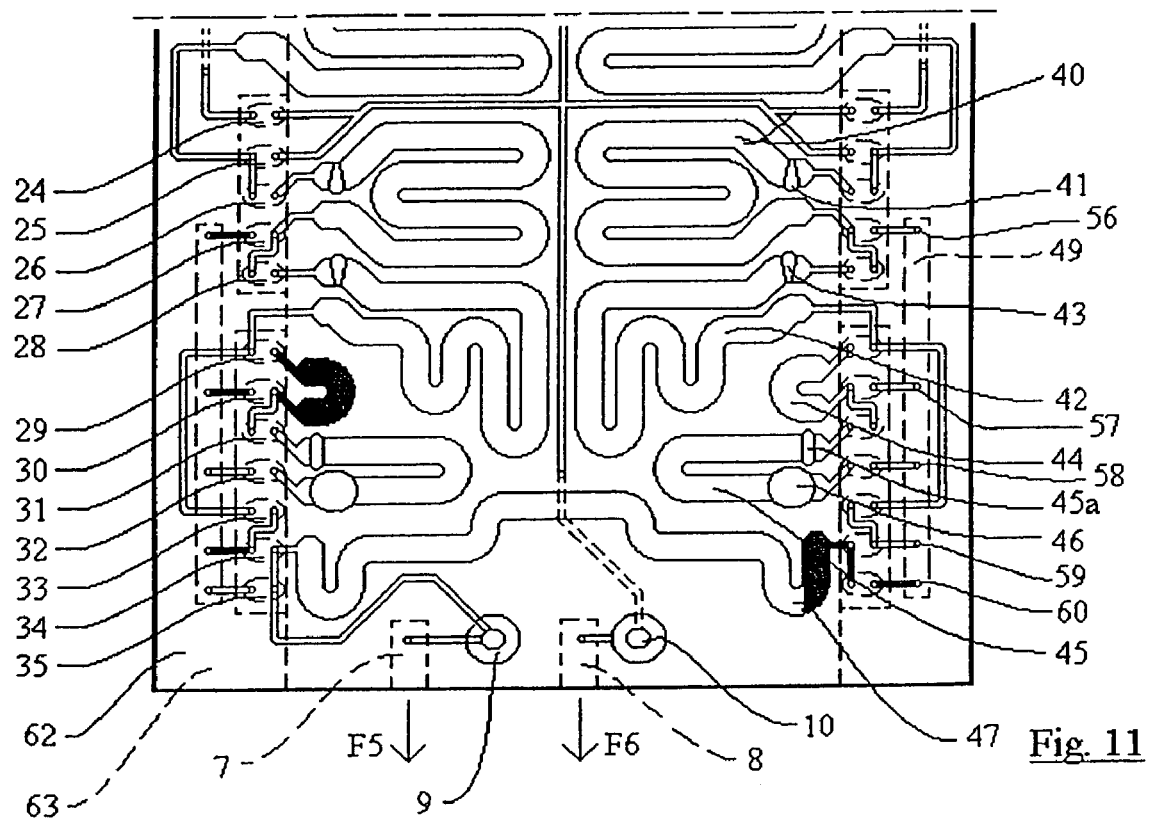
FIG. 11 represents a view identical to FIGS. 8 to 10, the elution fluid, which contains the nucleic acids and the functional and structural constituents and that was not transferred into the sampling compartment, being transferred into the convergence compartment, towards its discharge to the outside.
Figure 12:
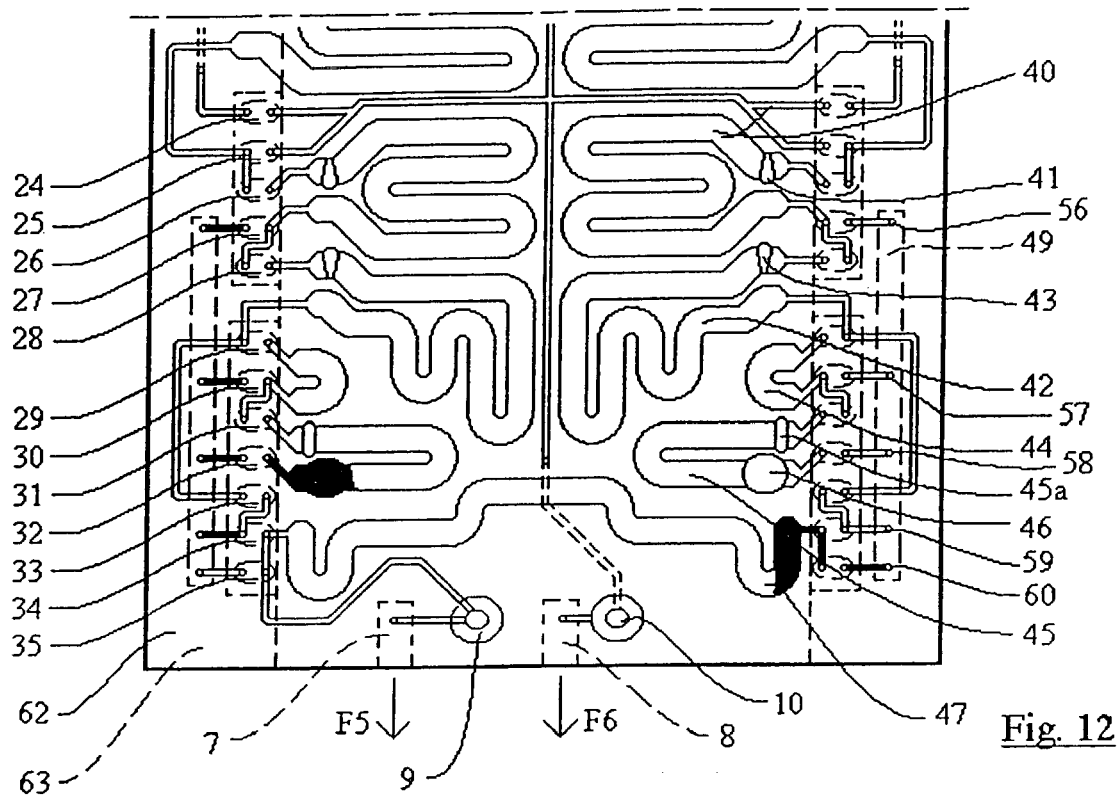
FIG. 12 represents a view identical to 8 to 11, the elution fluid, which is present in the sampling compartment, being transferred into the detection and reading compartment.
Figure 13:
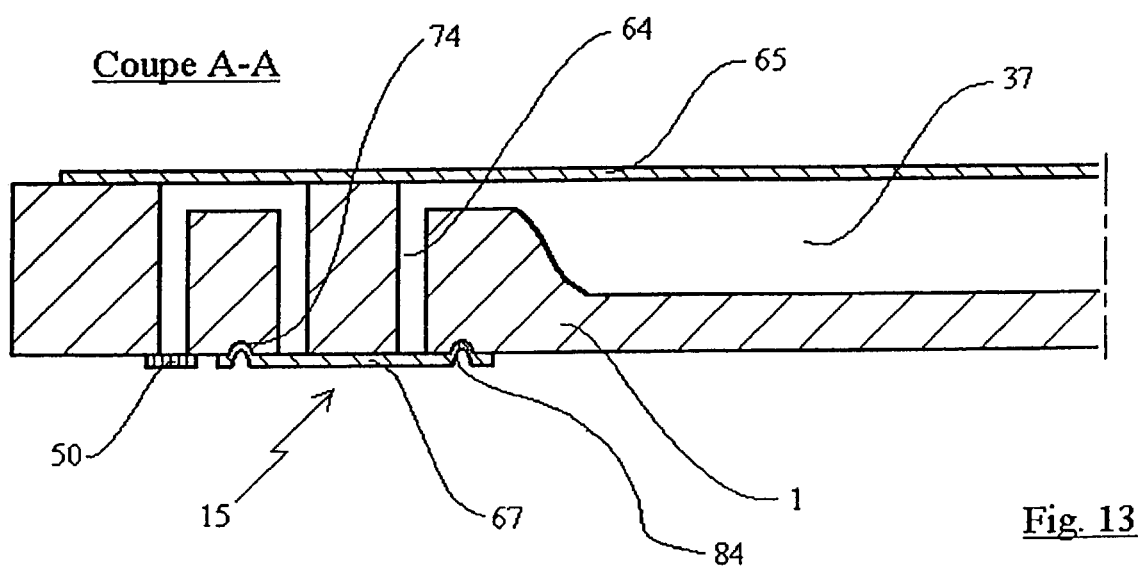
FIG. 13 shows a cross-sectional view through A-A in FIG. 3.
Figure 14:
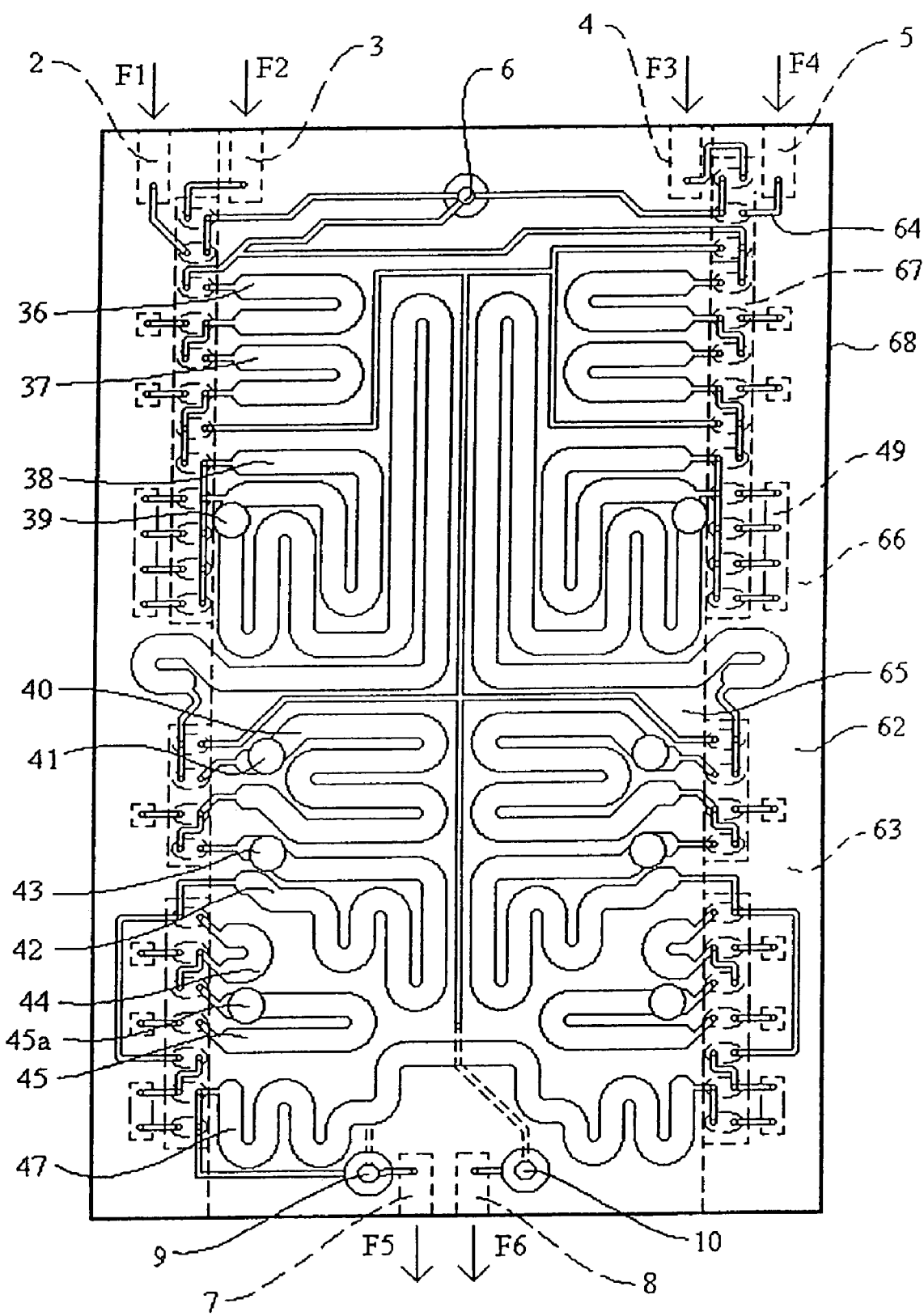
FIG. 14 represents a front view of the reaction card according to a second embodiment of the invention.

6th Step—Transfer of the Liquid Treated into the Sampling Compartment, into the Detection and Reading Compartment and into the Convergence Compartment:

During this sixth test, represented in FIGS. 10 to 12, three successive phases occur. These phases are as follows:
- the transfer of an initial part of the treated liquid 70, that is substantially 20 µl, containing or not containing the amplification product, from the functional constituent recovery compartment 42 to the sampling compartment 44, which corresponds to FIG. 10,
- the transfer of a second part of the treated liquid 70, corresponding to the remainder of said liquid 70, that is substantially 30 µl, from the functional constituent recovery compartment 42 to the convergence compartment 47, which corresponds to FIG. 11, and
- the transfer of this part of said treated liquid 70 from the sampling compartment 44 to the detection and reading compartment 45, which corresponds to FIG. 12.

According to FIG. 10, the following valves are closed:
- the inside orifice of the second valve 12,
- the outside orifice of the third valve 13,
- the outside orifice of the ninth valve 19,
- the inside orifice of at least one of the valves 20, 21, 22 and/or 23 and/or one of the orifices of the fourteenth valve 24,
- the inside orifice of the fifteen valve 25,
- the outside orifice of the twenty-first valve 31,
- the inside orifice of the twenty-fourth valve 34, and
- the inside orifice of the first valve 11 of the right-hand path.

This transfer allows the precise dosing of an aliquot of substantially 20 µl of treated solution 70, which will then be transferred into the detection and reading compartment 45. During this phase, the liquid 70 is stopped by a blocking filter 57, at the level of the detection and reading compartment 45, and a blocking filter 59, downstream from the convergence compartment 47.

According to FIG. 11, the closed valves are identical to the previous phase. Only the following differences are noted:
- opening of the inside orifice of the twenty-fourth valve 34,
- closure of the inside orifice of the twenty-fifth valve 35,
- closure of the outside orifice of the twenty-fourth valve 34 of the right-hand path, and
- closure of the inside orifice of the twenty-fifth valve 35 of the right-hand path.

As such, the transfer to the convergence compartment 47 is possible for the remainder of the treated liquid 70 which is not taken into consideration by the compartment 44. The blocking filter 60, associated with the twenty-fifth valve 35, stops this part of said liquid 70.

According to FIG. 12, the following valves are closed:
- the inside orifice of the second valve 12,
- the outside orifice of the third valve 13,
- the outside orifice of the ninth valve 19,
- the inside orifice of at least one of the valves 20, 21, 22 and/or 23 and/or one of the orifices of the fourteenth valve 24,
- the inside orifice of the fifteen valve 25,
- one of the orifices of the twenty-third valve 33, and
- the inside orifice of the first valve 11 of the right-hand path.

The nineteenth valve 29 is open, which allows the transfer to the detection and reading compartment 45 of the liquid 70, previously contained in the sampling compartment 44, possibly containing labelled amplicons. It should be noted that during this phase, the aliquot of said liquid 70 will pass through a zone upstream of said compartment 45 where a detection tablet 45a is located. Such a tablet 45a can contain, for example, amplicon cutting and labeling products, such as described in patent application PCT/FR99/01469 filed by the applicant on Jun. 17, 1999, under priority of Jun. 17, 1998.

The liquid 70 containing the amplicons possibly labelled and fragmented follows its movement and is stopped in the downstream portion of the compartment 45 by a blocking filter 58, such that said liquid 70 is present at the level of a reading cell 46. At this cell 46, it is possible to check that the amplification has been carried out and that the next phase can be performed. This amplification can be checked by means of unlabelled oligonucleotides, called capture probes, fixed at the level of the reading cell 46. These probes are adapted to be hybridised with the amplification product which had to be amplified, labelled and fragmented.

In another embodiment, the liquid 70 containing the unlabelled amplicons is stopped at the level of the cell 46. Amplification monitoring implements an unlabelled amplicon detection technique such as that described in:
- patent application WO-A-95/13399, WO-A-97/39008 or WO-A-99/64432, or patents U.S. Pat. No. 5,283,174, U.S. Pat. No. 5,656,207, U.S. Pat. No. 5,658,737 or U.S. Pat. No. 5,928,862, for similar techniques, and
- in the patent application WO-A-91/19812, or patents U.S. Pat. No. 4,889,798 or U.S. Pat. No. 5,998,135, for different techniques.

7$^{th}$ Step—Transfer of the Elution Liquid from the Convergence Compartment to the Outside:

The aliquot of treated liquid 70 in the convergence compartment 47 comes from the left-hand path of the card 1. Nonetheless, another aliquot 70, containing or not containing other specific amplicons due to amplification, can also be present coming from the right-hand path of the card 1. In the case of FIG. 12, the closed valves are identical but on the opposite paths. It is thus the blocking filter 35 of the right-hand side that enables the arrival of this aliquot to be stopped in the convergence compartment 47, and thus the mixing of said aliquots from both the right-hand and left-hand paths.

The amplifications in these two paths can be identical (identical buffers used), in order to obtain more amplicons, or different (through the use of different buffers), in order to allow several assays according to the number of different amplicons obtained.

It is also possible to have more than two paths in a reaction card 1 according to the invention. In this case, the channels 64 must be adapted to the vicinity of the inlet 6 and outlet 9 ball valves. In this way, it would be necessary to have other blocking filters and other valves in lower position in order to have all the aliquots converge into the compartment 47.

When the reading at the level of the cell 46 proves that the amplification has been carried out correctly, which proves the presence of a target in the initial biological sample, that is the test solution 69, the aliquot(s) present in the convergence compartment 47 are then transferred to another test sample card or reaction card, not shown in the figures, which allows the amplicons to be identified and analysed. It can use, for example, DNA chips developed by the Affymetrix Company, as described above. This transfer takes place through outlet 7, along F5, via the ball valve 9.

However, it is also possible that a biological chip be structurally integral with the reaction card 1. It is also possible that the sixth stage be limited to the transfer to the convergence compartment, without there being a control or amplification. Finally, this transfer can be performed directly in the DNA chip without passing through the convergence compartment.

REFERENCES

1. Reaction card
2. Entrance of the wash solution 71
3. Entrance of the test solution 69
4. Entrance of the elution liquid 72
5. Entrance for pressure variation inside the card 1
6. Card 1 entrance ball valve
7. Exit of the treated solution 70 to the outside
8. Waste outlet
9. Outside exit ball valve
10. Waste exit ball valve
11. First valve
12. Second valve
13. Third valve
14. Fourth valve
15. Fifth valve
16. Sixth valve
17. Seventh valve
18. Eighth valve
19. Ninth valve
20. Tenth valve
21. Eleventh valve
22. Twelfth valve
23. Thirteenth valve
24. Fourteenth valve
25. Fifteenth valve
26. Sixteenth valve
27. Seventeenth valve
28. Eighteenth valve
29. Nineteenth valve
30. Twentieth valve
31. Twenty-first valve 32. Twenty-second valve
33. Twenty-third valve
34. Twenty-fourth valve
35. Twenty-fifth valve
36. Test solution dosing compartment
37. Elution liquid dosing compartment
38. Separation compartment
39. Magnetic bead tablet
40. Structural constituent recovery compartment
41. Tablet of structural constituents enabling amplification to take place
42. Amplification compartment
43. Tablet of functional constituents enabling amplification to take place
44. Sampling compartment
45. Detection and reading compartment
45a. Detection tablet
46. Reading cell
47. Convergence compartment
48. First hydrophobic filter
49. Second hydrophobic filter
50. Blocking filter for a determined volume of elution liquid in the compartment 37
51. Blocking filter for a determined volume of the solution 70 in the compartment 36
52. Blocking filter of the test solution 70 in the compartment 38
53. Blocking filter of the first wash solution 71 in the compartment 38
54. Blocking filter of the second wash solution 71 in the compartment 38
55. Blocking filter of the elution liquid in the compartment 38
56. Blocking filter of the sample with the constituents in the compartment 40
57. Blocking filter of the sample in the reading cell 46
58. Blocking filter of the labelled sample in the compartment 45
59. Blocking filter of the sample with the enzymes in the compartment 42
60. Blocking filter of the sample with the enzymes in the compartment 47
61. Additional valve of the right-hand path, referred to as the purge valve
62. Front of the card 1
63. Rear of the card 1
64. Through channels on the front 62
65. Transparent film partitioning the channels 64 on the front 62
66. Transparent film partitioning the channels 64 on the rear 63
67. Transparent film partitioning the valves 11 to 35 and 61 on the rear 63
68. Side or edge of the card 1
69. Test solution
70. Treated solution
71. Wash solution
72. Elution liquid
73. Branch connection of the compartment 38 for blocking filters 52 to 55
74. Reinforcement or groove of each valve 11 to 35 and 61 where the film 67 is welded
75. Compression means of the film 67 or flexible tab
76. Hermetic closure means or elastomer pin
77. Opening apparatus or wedge
78. Strip assembly consisting of several tabs 75
79. Piston type actuator
80. Compressed air hose
81. Support
82. Beveled surface of the card 1
83. Blade 78 securing means
84. Peripheral weld located in the bottom of the groove 74
F1. Entrance of the wash solution 71
F2. Entrance of the test solution 70
F3. Entrance of the elution liquid
F4. Entrance for pressure variation inside the card 1
F5. Exit of the test solution to the outside
F6. Waste outlet
F7. Inlet of compressed air for actuating means 77
F8. Outlet of compressed air for actuating means 77
F9. Movement of actuating means 77
F10. Tipping of the tab 75

The invention claimed is:

1. A reaction card comprising a body, having a front surface and a rear surface connected by sides, at least one inlet and at least one outlet, connected one to the other through a network of channels constituting at least one reaction path for at least one fluid, the fluid or fluids being directed inside the card along the reaction path through a plurality of valves; each valve comprising a flexible film, which can be deformed to allow the fluid to pass through or which cooperates with a compression device to prevent the fluid from passing through, the flexible film being fixed on the rear surface of said card at a peripheral indentation of the assembly of channels associated with the valve; the card includes channels flush with at least one of its front and rear surfaces, the channels including at least some channels with a small cross-section for the transfer of fluid or fluids and some channels with a large cross-section serving as a reaction compartment; each front or rear surface is delimited by at least one film; the network of channels including a first set of channels providing a fluid conduit between the at least one inlet and a first compartment, a second set of channels providing a fluid conduit between the first compartment and a second compartment, a third set of channels providing a fluid conduit from the first compartment to the at least one outlet; and the valves including a first channel valve for controlling fluid flow from the first set of channels into the first compartment, and a second channel valve located at an output of the first compartment for controlling flow along the second set of channels and the third set of channels, the second channel valve having a first state where the valve is in one of either an open or closed position which permits fluid flow along the second set of channels and inhibits fluid flow along the third set of channels, and the second channel valve having a second state where the valve is in the other of the open or closed positions which inhibits fluid flow along the second set of channels and permits fluid flow along the third set of channels.

2. The card of claim 1, wherein the body of the card is monobloc, and wherein the compression device is affixed and integral with said card or forms a part of an apparatus allowing the card to be implemented.

3. The card of claim 1, wherein the ratio between the small cross-section and the large cross-section of the channels is between 1:1.01 and 1:10.

4. The card of claim 3, wherein said ratio is between 1:1.01 and 1.3.

5. The card of claim 1, wherein the channels are flush with all or part of the front surface of the card and the valves are present on the rear surface of said card.

6. The card of claim 1, wherein the front surface of the card includes a single film at a level of all the channels flush with this surface, and the rear surface of said card features:

at least a flexible film on the valves, at least a hydrophobic filter, and at least a film at a level of the channels flush with the rear surface.

7. The card of claim 6, wherein the flexible film(s) of the valve(s) and the film(s) of the rear surface make up a continuous layer to form a single film.

8. The card of claim 6, wherein said card is substantially parallelepiped-shaped, and the channels are, totally or in part, circumscribed in a middle part of the card, and further comprising blocking filters, associated with the hydrophobic filters, which are circumscribed at the level of at least one of the sides of said card, and the valves are positioned between the channels and the blocking filters.

9. The card of claim 1, wherein all of the inlets and outlets are formed in the sides of the card.

10. The card of claim 9, having a substantially parallelepiped shape, wherein the inlet or inlets are presented on one side, and the outlet or outlets are presented on another side.

11. The card of claim 10, wherein the inlet or inlets are presented on a side opposite the side where the outlet or outlets are presented.

12. The card of claim 11, having a substantially rectangular parallelepiped shape, wherein the inlet or inlets and the outlet or outlets are presented on opposite sides.

13. A reaction card comprising:

a body, having a front surface and a rear surface connected by sides, at least one inlet and at least one outlet, connected one to the other through a network of channels constituting at least one reaction path for at least one fluid, the fluid or fluids being directed inside the card along the reaction path via a plurality of valves, at least some of the channels formed in at least one of the front and rear surfaces, and at least one of the front or rear surface is delimited by at least one film;

each valve comprising a flexible film, which can be deformed to allow the fluid to pass through or which cooperates with a compression device to prevent the fluid from passing through, the flexible film being fixed on a surface of the card over an indentation formed in the card associated with the valve;

a first cavity formed in the body and defining a first compartment for receiving a volume of fluid; and a second cavity formed in the body and defining a second compartment;

the network of channels including a first set of channels defining a fluid conduit between the at least one inlet and the first compartment, a second set of channels defining a fluid conduit from the first compartment to the second compartment, and a third set of channels defining a fluid conduit for fluid to flow from the first compartment to the at least one outlet; and the valves including a first channel valve located within the first set of channels for controlling flow into the first compartment, and a second channel valve located at an output of the first compartment for controlling flow along the second set of channels and the third set of channels, the second channel valve having a first state where the valve is in one of either an open or closed position which permits fluid flow along the second set of channels and inhibits fluid flow along the third set of channels, and the second channel valve having a second state where the valve is in the other of the open or closed positions which inhibits fluid flow along the second set of channels and permits fluid flow along the third set of channels.

14. The card of claim 13, wherein the at least one inlet is a plurality of inlets for receiving a fluid supply, each inlet being potentially connectable to the first set of channels through one or more valves depending on the fluid to be supplied.

15. The card of claim 14, wherein at least one of the fourth set of channels is connected to the second channel valve.

16. The card of claim 13, wherein the at least one inlet includes a first inlet for supplying a fluid to be tested and a second inlet for supplying a wash solution, the second inlet being fluidly connected to at least the second compartment through a fourth set of channels and at least a third channel valve.

17. The card of claim 13, wherein there are a plurality of inlets, at least one of which is connected to a third compartment for receiving a volume of elution liquid, the third compartment being fluidly connected to the second compartment through one or more channels and a valve, the valve providing selective control of fluid flow into the second compartment from either the second set of channels or the channels from the third compartment.

18. The card of claim 17, wherein the second compartment includes a tablet of magnetic beads for separation of nucleic acids.

* * * * *